United States Patent
Carmichael et al.

(10) Patent No.: US 9,700,596 B2
(45) Date of Patent: Jul. 11, 2017

(54) LOCALLY RELEASED GROWTH FACTORS TO MEDIATE MOTOR RECOVERY AFTER STROKE

(75) Inventors: Stanley T. Carmichael, Sherman Oaks, CA (US); Andrew N. Clarkson, Dunedin (NZ)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/003,060

(22) PCT Filed: Mar. 1, 2012

(86) PCT No.: PCT/US2012/027278
§ 371 (c)(1),
(2), (4) Date: Dec. 11, 2013

(87) PCT Pub. No.: WO2012/121971
PCT Pub. Date: Sep. 13, 2012

(65) Prior Publication Data
US 2014/0315805 A1    Oct. 23, 2014

Related U.S. Application Data

(60) Provisional application No. 61/449,435, filed on Mar. 4, 2011.

(51) Int. Cl.
| | | |
|---|---|---|
| A61K 38/18 | (2006.01) | |
| A61K 31/728 | (2006.01) | |
| A61K 31/737 | (2006.01) | |
| A61K 9/00 | (2006.01) | |
| A61K 9/06 | (2006.01) | |
| A61K 47/36 | (2006.01) | |
| A61K 47/42 | (2017.01) | |
| A61L 27/38 | (2006.01) | |
| A61L 27/52 | (2006.01) | |
| A61L 27/54 | (2006.01) | |
| A61K 31/40 | (2006.01) | |
| A61K 31/445 | (2006.01) | |
| A61K 31/727 | (2006.01) | |

(52) U.S. Cl.
CPC .......... *A61K 38/185* (2013.01); *A61K 9/0085* (2013.01); *A61K 9/06* (2013.01); *A61K 31/40* (2013.01); *A61K 31/445* (2013.01); *A61K 31/727* (2013.01); *A61K 31/728* (2013.01); *A61K 31/737* (2013.01); *A61K 38/18* (2013.01); *A61K 47/36* (2013.01); *A61K 47/42* (2013.01); *A61L 27/3834* (2013.01); *A61L 27/52* (2013.01); *A61L 27/54* (2013.01); *A61L 2300/414* (2013.01); *A61L 2300/602* (2013.01); *A61L 2300/64* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 6,030,968 | A | 2/2000 | Gall et al. |
| 6,214,796 | B1 | 4/2001 | Finklestein et al. |
| 7,618,938 | B2 | 11/2009 | Li et al. |
| 7,862,826 | B2 | 1/2011 | Murphy et al. |
| 7,875,272 | B2 | 1/2011 | Messina et al. |
| 7,928,069 | B2 | 4/2011 | Prestwich et al. |
| 7,981,871 | B2 | 7/2011 | Prestwich et al. |
| 2001/0039261 | A1 | 11/2001 | Finklestein et al. |
| 2003/0022830 | A1 | 1/2003 | Charette et al. |
| 2006/0069009 | A1 | 3/2006 | Messina et al. |
| 2007/0123843 | A1 | 5/2007 | Gill et al. |
| 2009/0082263 | A1 | 3/2009 | Kaneda et al. |
| 2010/0285113 | A1 | 11/2010 | Shoichet et al. |

FOREIGN PATENT DOCUMENTS

| | | |
|---|---|---|
| CA | 2213906 A1 | 3/1998 |
| JP | 2005220070 A | 8/2005 |
| WO | WO 01/12236 | 2/2001 |
| WO | WO 02/063959 | 8/2002 |
| WO | WO 03/026489 | 4/2003 |
| WO | WO 2011/072399 | 6/2011 |

OTHER PUBLICATIONS

PCT International Search Report and Written Opinion dated Sep. 19, 2012 issued in PCT/US2012/027278.
PCT International Preliminary Report on Patentability dated Sep. 10, 2013 issued in PCT/US2012/027278.
Australian Patent Examination Report No. 1 dated Aug. 8, 2014 issued in AU 2012225784.
European Extended Search Report dated Jul. 31, 2014 issued in EP 12755443.4.
Arai et al. (2007) "Pharmacology of Ampakine Modulators: From AMPA Receptors to Synapses and Behavior" *Current Drug Targets*, 8: 583-602.
Ay et al. (1999) "Potential usefulness of basic fibroblast growth factor as a treatment for stroke," *Cerebrovasc Dis.*, 9: 131-5.
Bliss and Collingridge (1993) "A synaptic model of memory: long-term potentiation in the hippocampus," *Nature*, 361: 31-39.
Bramham (2008) "Local protein synthesis, actin dynamics, and LTP consolidation," *Curr. Opin. Neurobiol.*, 18: 524-531.
Braun et al. (1996) "Spatiotemporal relationship of apoptotic cell death to lymphomonocytic infiltration in photochemically induced focal ischemia of the rat cerebral cortex." *Acta. Neuropathol.*, 92(3):255-63.
Brown et al. (2007). "Extensive Turnover of Dendritic Spines and Vascular Remodeling in Cortical Tissues Recovering from Stroke," *J. Neurosci.*, 27: 4101-4109.

(Continued)

*Primary Examiner* — Robert C Hayes
(74) *Attorney, Agent, or Firm* — Tom Hunter; Weaver Austin Villeneuve & Sampson LLP

(57) ABSTRACT

Methods of improving recovery of a mammal after an ischemic event (e.g., stroke) are provided. In various embodiments the methods involve administering a neural growth factor (e.g., BDNF) into the infarct (e.g., stroke) cavity in a biocompatible hydrogel formulation. In certain embodiments the hydrogel comprises a thiolated hyaluronan and a thiolated gelatin with an optional thiolated heparin.

10 Claims, 16 Drawing Sheets

(56) References Cited

OTHER PUBLICATIONS

Brown et al. (2009) "In Vivo Voltage-Sensitive Dye Imaging in Adult Mice Reveals That Somatosensory Maps Lost to Stroke Are Replaced over Weeks by New Structural and Functional Circuits with Prolonged Modes of Activation within Both the Peri-Infarct Zone and Distant Sites," *J. Neurosci.*, 29: 1719-1734.
Carmeliet et al. (2002) "Vascular and neuronal effects of VEGF in the nervous system: implications for neurological disorders," *Semin Cell Dev Bioi* 13(1):39-53.
Carmichael (2006) "Cellular and molecular mechanisms of neural repair after stroke: Making waves" *Ann. Neurol.* 59(5):735-742.
Carmichael et al. (Oct. 20, 2009) "AMPAKine-mediated post-stroke functional improvements" *Abstracts of The Annual Meeting of The Society for Neuroscience. Society for Neuroscience.* Washington, DC, US. p. 639.2/Q9 [Presentation Abstract]. XP009179187.
Carmichael et al. (2001) "New patterns of intra-cortical connections after focal stroke," *Neurobiol. Dis.*, 8: 910-922.
Cheeran et al. (2008) "A common polymorphism in the brain-derived neurotrophic factor gene (BDNF) modulates human cortical plasticity and the response to rTMS," *J. Physiol.* 586: 5717-5725.
Clarkson and Carmichael (2009) "Cortical excitability and post-stroke recovery," *Biochem. Soc. Trans.*, 37(6): 1412-1414.
Clarkson et al. (2010) "Reducing excessive GABA-mediated tonic inhibition promotes functional recovery after stroke" *Nature* 468: 305-309 [LETTER—doi:10.1038/nature09511—7pages].
Conner et al. (2005) "The basal forebrain cholinergic system is essential for cortical plasticity and functional recovery following brain injury." *Neuron* 46(2): 173-179.
Croll et al. (2001) "Vascular growth factors in cerebral ischemia." *Mol Neurobiol* 23(2-3):121-135.
Derkach et al. (2007) "Regulatory mechanisms of AMPA receptors in synaptic plasticity" *Nat. Rev. Neurosci.* 8: 101-113.
Di Lazzaro et al. (2010) "Motor Cortex Plasticity Predicts Recovery in Acute Stroke" *Cereb. Cortex* 20: 1523-1528.
Dijkhuizen et al. (2003) "Correlation between Brain Reorganization, Ischemic Damage, and Neurologic Status after Transient Focal Cerebral Ischemia in Rats: A Functional Magnetic Resonance Imaging Study" *J. Neurosci.*, 23: 510-517.
Emerich et al. (2010) "Injectable VEGF hydrogels produce near complete neurological and anatomical protection following cerebral ischemia in rats" *Cell Transplant.* 19(9): 1063-1071.
Hermann et al., (Aug. 5, 2009) "Implications of vascular endothelial growth factor for postichemic neurovascular remodeling," *Journal of Cerebral Blood Flow and Metabolism* 29: 1620-1643.
Hummel and Cohen (2006) "Non-invasive brain stimulation: a new strategy to improve neurorehabilitation after stroke?" *Lancet Neurol.*, 5: 708-712.
Ji et al. (2010) "Acute and gradual increases in BDNF concentration elicit distinct signaling and functions in neurons" *Nat. Neurosci.*, 13(3): 302-309.
Kooijman et al. (2009) "Insulin-like growth factor 1: a potential neuroprotective compound for the treatment of acute ischemic stroke?" *Stroke* 40:e83-8.
Krakauer (2006) "Motor learning: its relevance to stroke recovery and neurorehabilitation" *Curr. Opin. Neurol.*, 19: 84-90.
Lauterborn et al. (2003) "Chronic elevation of brain-derived neurotrophic factor by ampakines" *J. Pharmacol. Exp. Ther.*, 307(1): 297-305.
Lauterborn et al. (2009) "Ampakines Cause Sustained Increases In Brain-Derived Neurotrophic Factor Signaling at Excitatory Synapses Without Changes in Ampa Receptor Subunit Expression Neuroscience" *Neuroscience* 159: 283-295.
Li et al. (2010) "An age-related sprouting transcriptome provides molecular control of axonal sprouting after stroke" *Nat. Neurosci.* 13: 1496-1504 [NIH Public Access—Author Manuscript 25 Pages].
Lipton (1999) "Ischemic Cell Death in Brain Neurons" *Physiol. Rev.* 79(4): 1431-1568.
Lynch et al. (2008) "The substrates of memory: Defects, treatments, and enhancement" *Eur. J. Pharmacol.* 585(1): 2-13.
Muller et al. (Jan. 31, 2008) "Brain-Derived Neurotrophic Factor But Not Forced Arm Use Improves Long-Term Outcome After Photothrombotic Stroke and Transiently Upregulates Binding Densities of Excitatory Glutamate Receptors in the Rat Brain" *Stroke* 39(3): 1012-1021.
Ohab et al. (2006) "A Neurovascular Niche for Neurogenesis after Stroke" *J. Neurosci.* 26: 13007-13016.
Peattie et al., (2008) "Effect of Gelatin on Heparin Regulation of Cytokine Release from Hyaluronan-Based Hydrogels," *Drug Delivery*15:389-397.
Ploughman, et al. (2009) "Brain-derived neurotrophic factor contributes to recovery of skilled reaching after focal ischemia in rats," *Stroke* 40(4):1490-5.
Prakash et al. (1996) "Rapid and opposite effects of BDNF and NGF on the functional organization of the adult cortex in vivo" *Nature* 381: 702-706.
Ren et al. (2005) "Growth factor treatment of stroke." *Curr Drug Targets CNS Neurol Disord* 4:121-5.
Schabitz et al. (2004) "Effect of Brain-Derived Neurotrophic Factor Treatment and Forced Arm Use on Functional Motor Recovery After Small Cortical Ischemia" *Stroke* 35: 992-997.
Schabitz, et al. (2007) "Intravenous brainderived neurotrophic factor enhances poststroke sensorimotor recovery and stimulates neurogenesis." *Stroke* 38(7):2165-2172.
Sigler et al. (2009) "Imaging rapid redistribution of sensory-evoked depolarization through existing cortical pathways after targeted stroke in mice" *Proc. Natl. Acad. Sci. U.S.A.*, 106(28): 11759-11764.
Simmons et al. (2009) "Up-regulating BDNF with an ampakine rescues synaptic plasticity and memory in Huntington's disease knockin mice" *Proc. Natl. Acad. Sci. U.S.A.*, 106(12): 4906-4911.
Szenasi, et al. (Dec. 12, 2007) "2.3-Benzodiazepine-type AMPA receptor antagonists and their neuroprotective effects" *Neurochemistry International—Pergamon Press.* Oxford. Gb 52(1-2): 166-183.
Tabakman et al. (2005) "Neuroprotection by NGF in the PC12 in vitro OGD model: involvement of mitogen-activated protein kinases and gene expression." *Ann N Y Acad Sci* 1053:84-96.
Wang et al. (2006) "Viral vector strategy for glial cell line-derived neurotrophic factor therapy for stroke." *Front Biosci.* 11:1101-7. [Downloaded from https://www.bioscience.org/2006/v11/af/1866/2.htm on Oct. 20, 2014; 11 pages].
Weiser (2005) "AMPA Receptor Antagonists for the Treatment of Stroke" *Curr. Drug Targets CNS Neurol. Disord.* 4(2): 153-159.
Wu (2005) "Neuroprotection in experimental stroke with targeted neurotrophins." *NeuroRx* 2:120-8.
Zhang and Pardridge (2006) "Blood-brain barrier targeting of BDNF improves motor function in rats with middle cerebral artery occlusion." *Brain Res.*, 1111(1): 227-229.
European Extended Search Report dated Oct. 13, 2014 issued in EP 14171183.8.
Chen et al. (2006) "Neurorestorative Treatment of Stroke: Cell and Pharmacological Approaches," *Journal of the American Society for Experimental Neurotherapeutics* 3(4): 466-473.
Horie et al. (2011) "Transplanted Stem Cell-Secreted Vascular Endothelial Growth Factor Effects Poststroke Recovery, Inflammation, and Vascular Repair," *Stem Cells* 29(2): 274-285.
Ikeda et al. (2005) "Bone Marrow Stromal Cells That Enhanced Fibroblast Growth Factor-2 Secretion by Herpes Simplex Virus Vector Improve Neurological Outcome After Transient Focal Cerebral Ischemia in Rats," *Stroke* 36(12): 2725-2730.
Johnston et al. (2001) "Trophic factor secreting kidney cell lines: in vitro characterization and functional effects following transplantation in ischemic rats," *Brain Research* 900(2): 268-276.
Kurozumi et al. (2005) "Mesenchymal Stem Cells That Produce Neurotrophic Factors Reduce Ischemic Damage in the Rat Middle Cerebral Artery Occlusion Model," *Molecular Therapy* 11(1): 96-104.

(56) References Cited

OTHER PUBLICATIONS

Lim et al. (2012) "The effect of injectable gelatin-hydroxyphenylpropionic acid hydrogel matrices on the proliferation, migration, differentiation and oxidative stress resistance of adult neural stem cells," *Biomaterials* 33(12): 3446-3455.

Mahoney et al. (2006) "Three-dimensional growth and function of neural tissue in degradable polyethylene glycol hydrogels," *Biomaterials* 27(10): 2265-2274.

Miki et al. (2007) "Vascular Endothelial Growth Factor Gene-Transferred Bone Marrow Stromal Cells Engineered with a Herpes Simplex Virus Type 1 Vector Can Improve Neurological Deficits and Reduce Infarction Volume in Rat Brain Ischemia," *Neurosurgery* 61(3): 586-595.

Prestwich (2011) "Hyaluronic acid-based clinical biomaterials derived for cell and molecule delivery in regenerative medicine," *Journal of Controlled Release* 155(2): 193-199.

Seidlits et al. (2010) "The effects of hyaluronic acid hydrogels with tunable mechanical properties on neural progenitor cell differentiation," *Biomaterials* 31(14): 3930-3940.

Takahashi et al. (2008) "Embryonic neural stem cells transplanted in middle cerebral artery occlusion model of rats demonstrated potent therapeutic effects, compared to adult neural stem cells," *Brain Research* 1234: 172-182.

Zhong et al. (2010) "Hydrogel Matrix to Support Stem Cell Survival After Brain Transplantation in Stroke," *Neurorehabilitation and Neural Repair* 24(7): 636-644.

An et al. (2015) Defining the ischemic penumbra using magnetic resonance oxygen metabolic index. Stroke 46(4): 982-988.

Baron et al. (2014) Selective neuronal loss in ischemic stroke and cerebrovascular disease. J. Cereb. Blood Flow Metab. 34(1): 2-18.

Bible et al. (2009) The support of neural stem cells transplanted into stroke-induced brain cavities by PLGA particles. Biomaterials, 30: 2985-2994.

Carmichael (2010) Targets for neural repair therapies after stroke. Stroke, 41(10 Suppl): S124-126.

Cramer (2014) Drugs to Enhance Motor Recovery After Stroke. Stroke, 46(10): 2998-3005.

Fisher (1997) Characterizing the target of acute stroke therapy. Stroke, 28(4): 866-872.

Garcia et al. (1996) Ischemic Stroke and Incomplete Infarction. Stroke 27: 761-765.

Greenberg and Jin (2006) Growth Factors and Stroke, NeuroRx, 3: 458-465.

Heiss et al. (1992) Progressive derangement of periinfarct viable tissue in ischemic stroke. J. Cereb. Blood Flow Metab. 112(2): 193-203.

Heiss et al. (2012) Ann. N.Y. Acad. Sci. 1268: 26-34.

Jin et al. (2010) Delayed transplantation of human neural precursor cells improves outcome from focal cerebral ischemia in aged rats. Aging Cell, 9: 1076-1083.

Jin et al. (2010) Transplantation of human neural precursor cells in Matrigel scaffolding improves outcome from focal cerebral ischemia after delayed postischemic treatment in rats, J. Cereb. Blood Flow Metabl. 30: 534-544.

Jin et al. (2011) Effect of human neural precursor cell transplantation on endogenous neurogenesis after focal cerebral ischemia in the rat. Brain Res., 1374: 56-62.

Paciaroni et al. (2009) The concept of ischemic penumbra in acute stroke and therapeutic opportunities. Eur Neurol. 61(6): 321-330.

Park et al. (2002) The injured brain interacts reciprocally with neural stem cells supported by scaffolds to reconstitute lost tissue, Nat. Biotechnol., 20: 111-1117.

Schrandt et al. (2015) Chronic monitoring of vascular progression after ischemic stroke using multiexposure speckle imaging and two-photon fluorescence microscopy. J. Cereb. Blood Flow Metab. 35(6): 933-942.

Schroeter et al. (2009) Neuroinflammation extends brain tissue at risk to vital peri-infarct tissue: a double tracer [11C]PK11195- and [18F]FDG-PET study. J. Cereb Blood Flow Metabol. 29: 1216-1225.

Torack (1982) Computed tomography and stroke edema: case report with an analysis of water in acute infarction. Comput Radiol. 6(1):35-41.

Australian Patent Examination Report No. 2 dated Oct. 6, 2015 issued in AU 2012225784.

Bogousslaysky et al. (2002) "Fiblast (trafermin) in acute stroke: results of the European-Australian phase II/III safety and efficacy trial." *Cerebrovasc Dis.* 14(3-4): 239-251.

Carmichael (2012) "Brain Excitability in Stroke: The Yin and Yang of Stroke Progression" *Arch. Neurol.* 69(2): 161-167 [HHS Public Access—Author manuscript—13 pages].

Cook et al. (May 12, 2016) "Hydrogel-delivered brain-derived neurotrophic factor promotes tissue repair and recovery after stroke" *J. Cereb. Blood Flow Metab* pii: 0271678X16649964 [Epub ahead of print], 16 pages.

Dobkin and Carmichael (2016) "The Specific Requirements of Neural Repair Trials for Stroke." *Neurorehabil. Neural Repair*, 30(5): 470-478.

Overman et al. (2012) "A role for ephrin-A5 in axonal sprouting, recovery, and activity-dependent plasticity after stroke" *Proc. Natl. Acad. Sci. USA*, 109(33): 13154-13155.

Park and Poo (Jan. 2013) "Neurotrophin regulation of neural circuit development and function" *Nat. Rev. Neurosci.*, 14(1): 7-23.

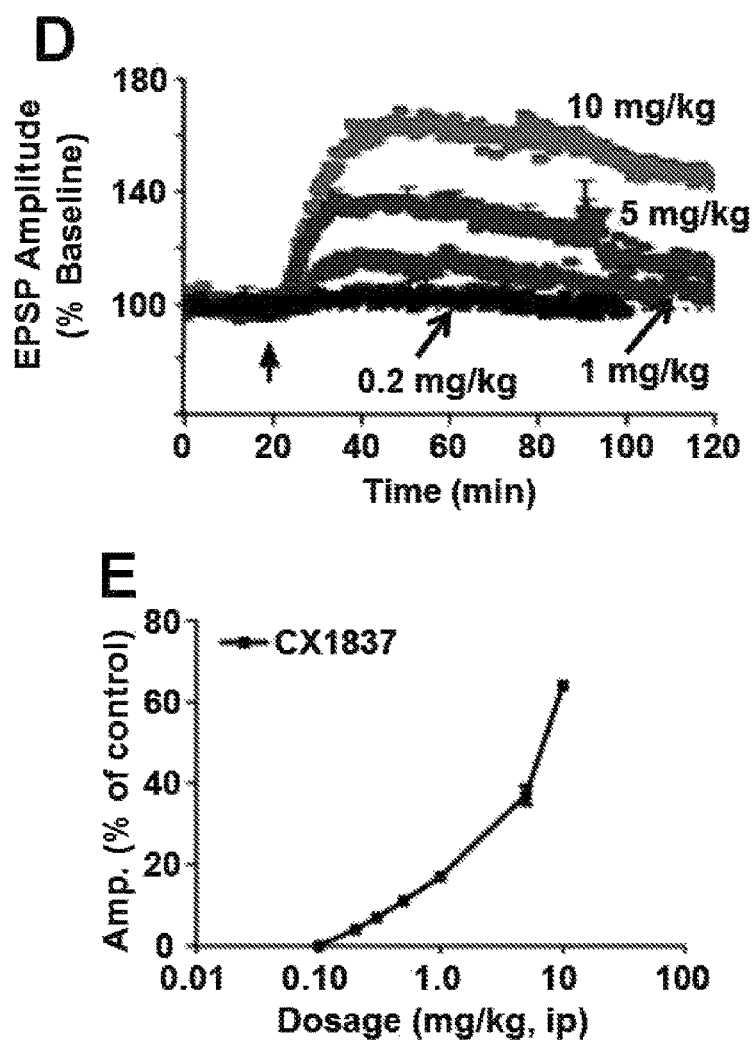
*Fig. 4, cont'd.*

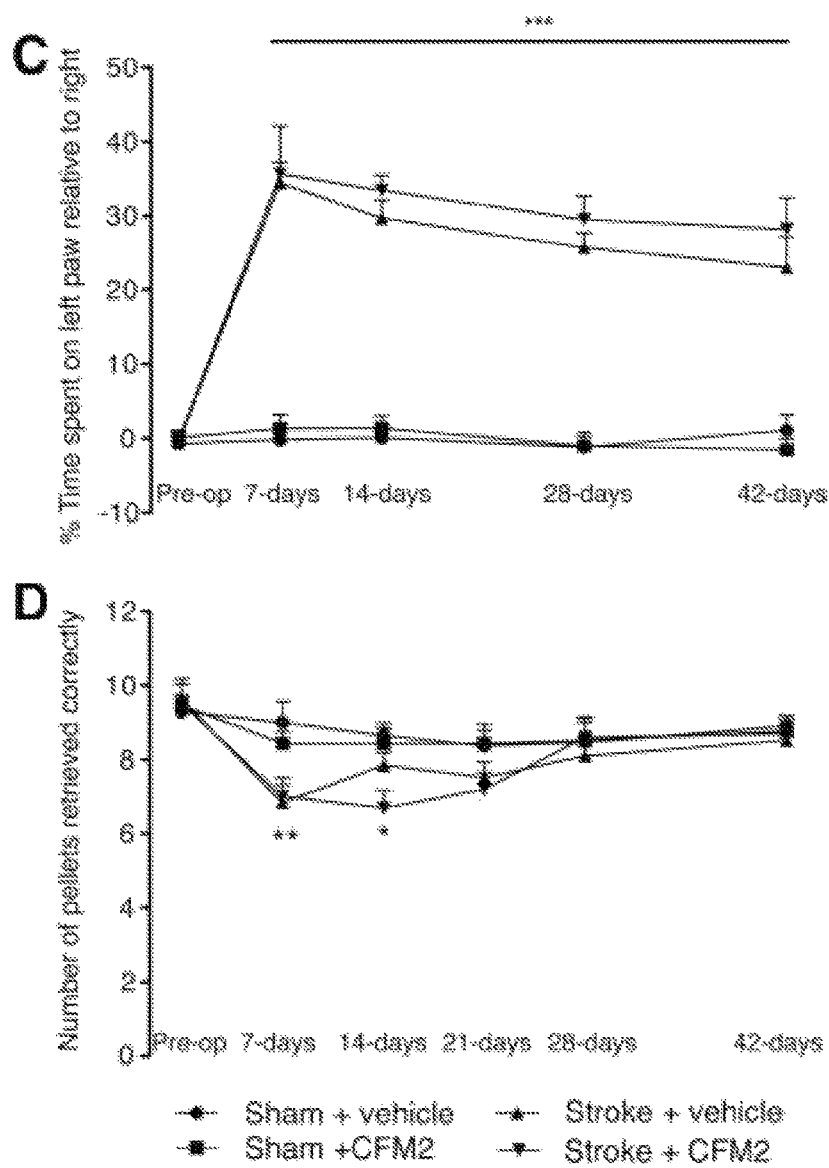
Fig. 7, cont'd.

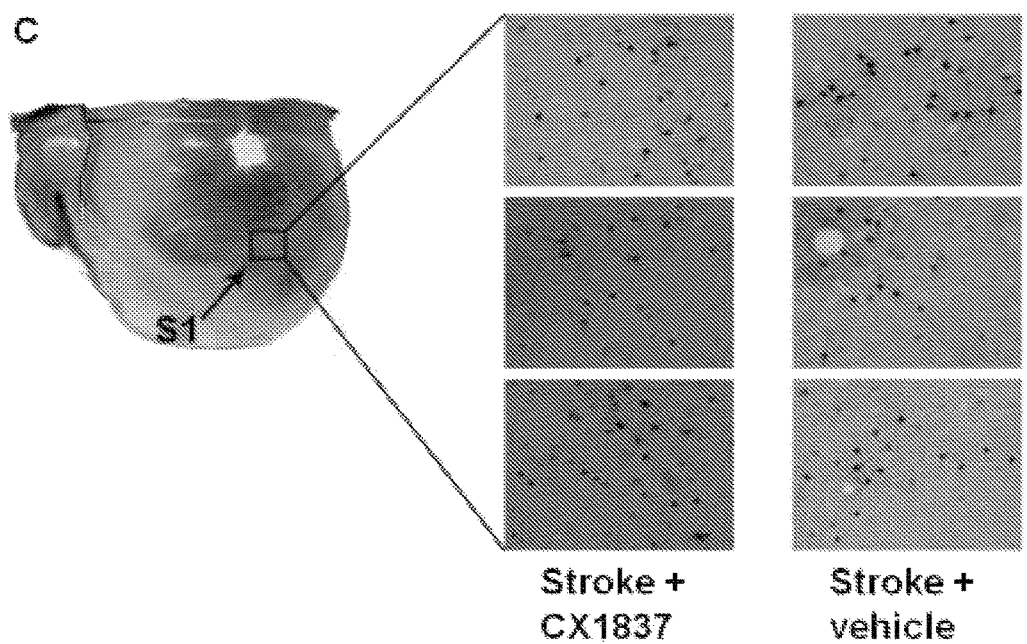
*Fig. 8, cont'd.*

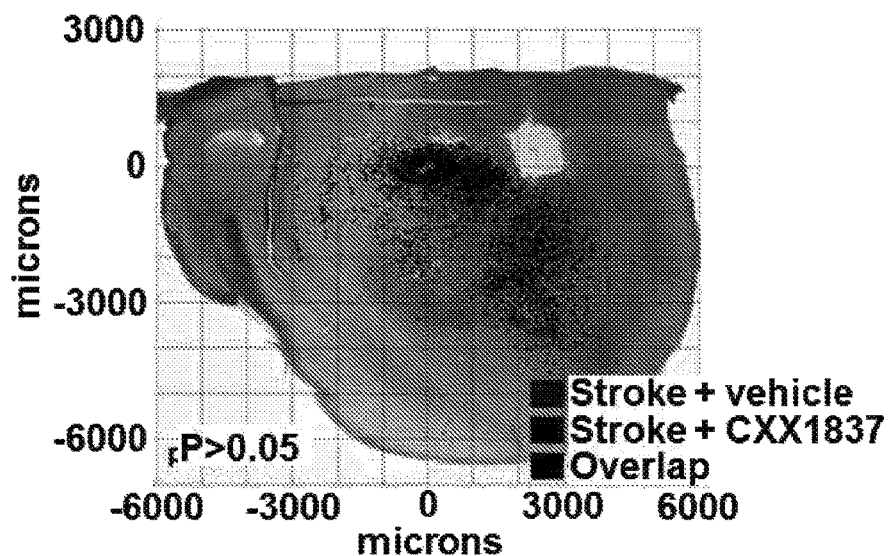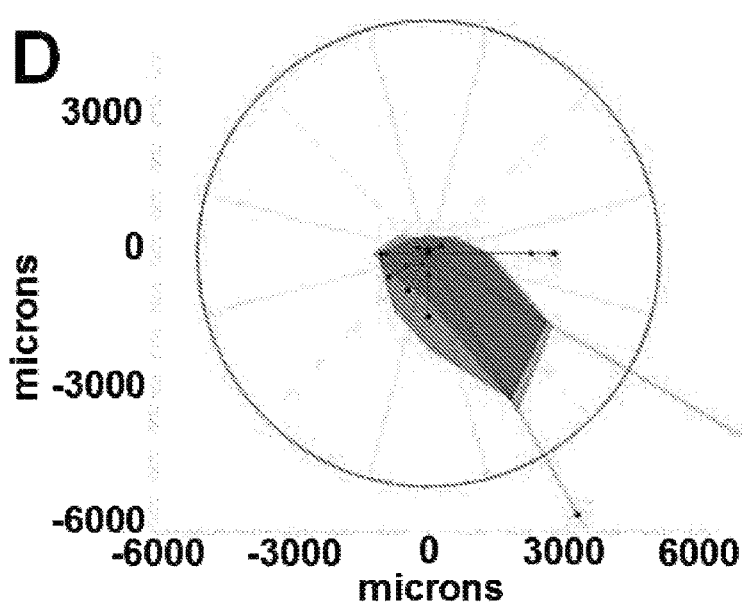
*Fig. 9, cont'd.*

LOCALLY RELEASED GROWTH FACTORS TO MEDIATE MOTOR RECOVERY AFTER STROKE

CROSS-REFERENCE TO RELATED APPLICATIONS

This application is a 371 National Phase of PCT/US2012/027278, filed on Mar. 1, 2012, which claims benefit of and priority to U.S. Ser. No. 61/449,435, filed on Mar. 4, 2011, which is incorporated herein by reference in its entirety for all purposes.

STATEMENT OF GOVERNMENTAL SUPPORT

[Not Applicable]

BACKGROUND

Stroke is the leading cause of adult disability in developed countries. There is no therapy that targets the promotion of stroke recovery. As present the only stroke therapy is the administration of tissue plasminogen activator (tPA). TPA is a "clot busting" drug that does not target stroke recovery, but targets the blood vessel that is obstructed in stroke. TPA must be given within 4.5 hours after stroke because if given later it will cause bleeding into the brain. There is no stroke therapy that can be given at a time point later than 4.5 hours. There is no stroke therapy that targets the processes of tissue repair and not the vessel that is obstructed.

SUMMARY

The methods described herein pertain to methods to facilitate recovery after brain injury, such acute brain injury in stroke or traumatic brain injury, or chronic brain injury such as in a neurodegenerative disease. In various embodiments the methods involve the release of a growth factor(s) (e.g., BDNF) directly to the area of repair and recovery in the brain, for a short period of time, using a biocompatible device, such as a hydrogel delivery device or a nanoparticle. This approach is unique and better compared to previous BDNF or growth factor(s) delivery approaches for five reasons. The growth factor(s) (e.g., BDNF) delivery is locally done within a specific region of the brain in a site directly adjacent to its intended brain target. The biocompatible device delivers growth factor(s) (e.g., BDNF) in a way that bypasses the blood brain barrier and provides a sustained, timed release. The release of growth factor(s) (e.g., BDNF) from the device occurs for one month after stroke, after just one injection of the device. The device delivers the growth factor(s)(s) in a way that does not promote inflammation or tissue damage. The device can be injected using very small delivery needles that minimize brain damage.

In certain embodiments methods for improving recovery (e.g., motor recovery) of a mammal after cerebral ischemia are provided. The methods typically involve administering a therapeutically effective amount of a brain growth factor to the infarct cavity in the brain of the mammal. In certain embodiments the improvement in motor recovery comprises an improvement in motor coordination, and/or balance, and/or speech. In certain embodiments the improvement is an improvement in the degree of recovered function and/or the rate of recovery of function. In certain embodiments the administering comprises depositing a depot delivery system into the infarct cavity where the depot delivery system comprises the growth factor and provides sustained release of the growth factor, and/or the depot delivery system comprises cells that provide a sustained release of the brain growth factor. In various embodiments the depot delivery system comprises a delivery system selected from the group consisting of a nanoparticle formulation, a hydrogel formulation, and an implantable mechanical delivery system. In certain embodiments the depot delivery system comprises a hydrogel comprising the growth factor and/or the cells (e.g., a hydrogel depot formulation). In certain embodiments the hydrogel comprises a biopolymer. In certain embodiments the hydrogel comprises one or more materials selected from the group consisting of thiol-modified hyaluronan, thiol-modified heparin, a hyaluronan sodium salt, an acrylated hyaluronic acid, and cross-linker peptides. In certain embodiments the hydrogel comprises hyaluronan and gelatin or a hyaluronan derivative and/or a gelatin derivative (e.g., a thiolated hyaluronan and/or a thiolated gelatin). In certain embodiments the hyaluronan and the gelatin are have each been thiol-modified using carbodiimide mediated hydrazide chemistry. In certain embodiments the hyaluronan and gelatin or hyaluronan derivative and/or gelatin derivative are crosslinked. In certain embodiments they are crosslinked using a divalent or polyvalent (e.g., trivalent, tetravalent, pentavalent, etc.) electrophile. In certain embodiments the derivatives of hyaluronan and gelatin are crosslinked with a reagent selected from the group consisting of a polyethylene glycol diacrylate (PEGDA), a polyethylene glycol divinyl sulfone, a polyethylene glycol bismaleimide, a polyethylene glycol dimethyacrylate, a polyethylene glycol (methyl)acrylamide, and a polyethylene glycol di(halo) acetate. In certain embodiments the hyaluronan (or hyaluronan derivative) and gelatin (or gelatin derivative) are crosslinked with a polyethylene glycol diacrylate (PEGDA) linker. In certain embodiments the hydrogel further comprises a heparin or heparin derivative (e.g., a thiol-modified heparin). In certain embodiments the heparin or heparin derivative is linked to the hyaluronan and/or to the gelatin (or to a hyaluronan derivative and/or a gelatin derivative). In certain embodiments the heparin derivative is linked to the hyaluronan derivative and/or to the gelatin derivative with a divalent or polyvalent (e.g., trivalent, tetravalent, pentavalent, etc.) electrophile. In certain embodiments the heparin derivative is linked to the hyaluronan derivative and/or to the gelatin derivative with a reagent selected from the group consisting of a polyethylene glycol diacrylate (PEGDA), a polyethylene glycol divinyl sulfone, a polyethylene glycol bismaleimide, a polyethylene glycol dimethyacrylate, a polyethylene glycol (methyl)acrylamide, and a polyethylene glycol di(halo)acetate. In certain embodiments the heparin derivative is linked to the hyaluronan derivative and/or to the gelatin derivative with a polyethylene glycol diacrylate (PEGDA) linker. In certain embodiments the hydrogel comprises at most about 10% solids w/v, or at most about 5% solids w/v, or at most about 4% solids w/v, or at most about 2% solids w/v, or at most about 1% solids w/v. In certain embodiments the depot delivery system comprises a hydrogel containing the growth factor(s) where the hydrogel and provides sustained release of the growth factor (e.g., over at least one day, or over at least 2 days, or over at least about 3 days, or over at least about 5 days, or over at least about 1 week, or over at least about 2 weeks, or over at least about 3 weeks, or over at least about 4 weeks, or over at least about 5 weeks, or over at least about 6 weeks, or over at least about 2 months). In certain embodiments the brain growth factor comprises one or more factors selected from the group consisting of BDNF, VEGF, IGF1, bFGF/FGF2, Ang1, Ang 2, BMP 2, BMP 3a, BMP 3b, BMP 4, BMP 5, BMP 6, BMP 7 (OP-1), CTNF, EGF, EPO, aFGF/FGF1, bFGF/FGF2, G-CSF, GDF10, GDF15, GDNF, GH, GM-CSF, HB-EGF, LIF, NGF, NT-3, NT 4/5, Osteopontin, PDGFaa, PDGFbb, PDGFab, P1GF, SCF, SDF1/CXCL12, and TGFβ. In certain embodiments the brain growth factor comprises one or more factors selected from the group consisting of BDNF, VEGF, IGF-1, and bFGF. In certain embodiments the brain growth factor comprises BDNF. In certain embodiments the depot delivery system comprises a hydrogel comprising cells that provide a sustained release of the brain growth factor. In certain embodiments the cells comprise stem cells (e.g., adult stem cells, embryonic stem cells, cord stem cells, and induced pluripotent stem cells (IPSCs), and the like). In certain embodiments the cells are cells that have differentiated from stem cells in culture or after implantation into the mammal. In certain embodiments the cells are derived from cells/cell lines selected from the group consisting of SM22, CM02, E33, 7PEND24, B16, C4ELS5.1, T36, E68, T43, W10, and EN13. In certain embodiments the cells are derived from cells/cell lines selected from the group consisting of SM22, CM02, E33, and EN13. In certain embodiments the cells express and secrete one or more factors selected from the group consisting of BDNF, VEGF, IGF1, bFGF/FGF2, Ang1, Ang 2, BMP 2, BMP 3a, BMP 3b, BMP 4, BMP 5, BMP 6, BMP 7 (OP-1), CTNF, EGF, EPO, aFGF/FGF1, bFGF/FGF2, G-CSF, GDF10, GDF15, GDNF, GH, GM-CSF, HB-EGF, LIF, NGF, NT-3, NT 4/5, Osteopontin, PDGFaa, PDGFbb, PDGFab, P1GF, SCF, SDF1/CXCL12, and TGFβ. In certain embodiments the cells secrete one or more factors selected from the group consisting of BDNF, HBEGF, VEGF, IGF-1, and bFGF. In certain embodiments the cells secrete BDNF. In certain embodiments BDNF expression by the cells is enhanced by culturing the cells in the presence of neuronal media.

In various embodiments the administering comprises injecting the depot formulation into the ischemic cavity. In certain embodiments the depot delivery system is not administered until AMPAR signaling switches from promoting cell death to promoting behavioral recovery. In certain embodiments the depot delivery system is not administered within the first hour, or not administered within the first three hours, or not administered within the first 6 hours, or not administered within the first 12 hours, or not administered within the first 24 hours after the onset of the ischemic event. In certain embodiments the depot delivery system is administered after at least 24 hours after the onset of the ischemic event, or after at 2 days after the onset of the ischemic event, or after at least 3 days after the onset of the ischemic event, or after at least 4 or 5 days after the onset of the ischemic event, or after at least 7 days after the onset of the ischemic event. In certain embodiments the depot delivery system is administered within one week of the onset of the ischemic event. In certain embodiments the depot delivery system is administered after the subject is clinically stable from the ischemia and damage has substantially stopped progressing. In certain embodiments the depot delivery system is initially administered after at least 3 days, or at least five or more days, after the initial ischemic event. In certain embodiments the depot delivery system is administered up to about 1 year, or up to about 1.5 years, or up to about 2 years after the initial ischemic event. In certain embodiments mammal is a human. In certain embodiments the mammal is a non-human mammal.

In certain embodiments formulations for improving recovery of a mammal after cerebral ischemia are provided. The formulations typically comprise a hydrogel comprising one or more brain growth factors that, where when the formulation is placed in an infarct cavity in the brain of a mammal, provides sustained release of the growth factor over at least about one week; and/or a hydrogel comprising cells that provide a sustained release of a brain growth factor over a period of at least about one week, or at least about two weeks, or at least about three weeks. In certain embodiments the hydrogel comprises hyaluronan and gelatin and/or a hyaluronan derivative and/or a gelatin derivative. In certain embodiments the hyaluronan and the gelatin are each thiolated. In certain embodiments the hyaluronan and the gelatin have each been thiol-modified using carbodiimide mediated hydrazide chemistry. In certain embodiments the hyaluronan derivative and gelatin derivative are crosslinked. In certain embodiments the derivatives of hyaluronan and gelatin are crosslinked with a divalent or polyvalent electrophile. In certain embodiments the derivatives of hyaluronan and gelatin are crosslinked with a reagent selected from the group consisting of a polyethylene glycol diacrylate (PEGDA), a polyethylene glycol divinyl sulfone, a polyethylene glycol bismaleimide, a polyethylene glycol dimethyacrylate, a polyethylene glycol (methyl)acrylamide, and a polyethylene glycol di(halo)acetate. In certain embodiments the hyaluronan derivative h is linked to the gelatin derivative with a divalent or polyvalent electrophile. In certain embodiments the hyaluronan derivative is linked to the gelatin derivative with a reagent selected from the group consisting of a polyethylene glycol diacrylate (PEGDA), a polyethylene glycol divinyl sulfone, a polyethylene glycol bismaleimide, a polyethylene glycol dimethyacrylate, a polyethylene glycol (methyl)acrylamide, and a polyethylene glycol di(halo)acetate. In certain embodiments the hyaluronan derivative and gelatin derivative are crosslinked with a polyethylene glycol diacrylate (PEGDA) linker. In certain embodiments the hydrogel further comprises a heparin derivative. In certain embodiments the heparin derivative is a thiol-modified heparin. In certain embodiments the heparin derivative is linked to the hyaluronan derivative and/or to the gelatin derivative. In certain embodiments the heparin derivative is linked to the hyaluronan derivative and/or to the gelatin derivative with a divalent or polyvalent electrophile. In certain embodiments the heparin derivative is linked to the hyaluronan derivative and/or to the gelatin derivative with a reagent selected from the group consisting of a polyethylene glycol diacrylate (PEGDA), a polyethylene glycol divinyl sulfone, a polyethylene glycol bismaleimide, a polyethylene glycol dimethyacrylate, a polyethylene glycol (methyl)acrylamide, and a polyethylene glycol di(halo)acetate. In certain embodiments the heparin derivative is linked to the hyaluronan and/or to the gelatin with a polyethylene glycol diacrylate (PEGDA) linker. In certain embodiments the hydrogel comprises at most about 10% solids w/v, or at most about 5% solids w/v, or at most about 3% solids w/v, or at most about 2% solids w/v. In certain embodiments the formulation comprises a hydrogel comprising one or more brain growth factors that, when placed in an infarct cavity in the brain of a mammal, provides sustained release of the growth factor over at least about one week. In certain embodiments the brain growth factor comprises one or more factors selected from the group consisting of BDNF, VEGF, IGF1, bFGF/FGF2, Ang1, Ang 2, BMP 2, BMP 3a, BMP 3b, BMP 4, BMP 5, BMP 6, BMP 7 (OP-1), CTNF, EGF, EPO, aFGF/FGF1, bFGF/FGF2, G-CSF, GDF10, GDF15, GDNF, GH, GM-CSF, HB-EGF, LIF, NGF, NT-3, NT 4/5, Osteopontin, PDGFaa, PDGFbb, PDGFab, P1GF, SCF, SDF1/CXCL12, and TGFβ. In certain embodiments the brain growth factor comprises one or more factors selected from the group consisting of BDNF, VEGF, IGF-1, and bFGF. In certain embodiments the brain growth factor comprises BDNF. In certain embodiments the formulation comprises a hydrogel comprising cells that provide a sustained release of a brain growth factor over a period of at least about one week. In certain embodiments the cells comprise stem cells (e.g., adult stem cells, embryonic stem cells, cord stem cells, and induced pluripotent stem cells (IPSCs), and the like). In certain embodiments the cells are cells that have differentiated from stem cells in culture or after implantation into the mammal. In certain embodiments the cells are derived from cells/cell lines selected from the group consisting of SM22, CM02, E33, 7PEND24, B16, C4ELS5.1, T36, E68, T43, W10, and EN13. In certain embodiments the cells are derived from cells/cell lines selected from the group consisting of SM22, CM02, E33, and EN13. In certain embodiments the cells secrete one or more factors selected from the group consisting of BDNF, VEGF, IGF1, bFGF/FGF2, Ang1, Ang 2, BMP 2, BMP 3a, BMP 3b, BMP 4, BMP 5, BMP 6, BMP 7 (OP-1), CTNF, EGF, EPO, aFGF/FGF1, bFGF/FGF2, G-CSF, GDF10, GDF15, GDNF, GH, GM-CSF, HB-EGF, LIF, NGF, NT-3, NT 4/5, Osteopontin, PDGF-AA, PDGF-BB, PDGF-AB, P1GF, SCF, SDF1/CXCL12, and TGFβ. In certain embodiments the cells secrete one or more factors selected from the group consisting of BDNF, HBEGF, VEGF, IGF-1, and bFGF. In certain embodiments the cells secrete BDNF. In certain embodiments BDNF expression by the cells is enhanced by culturing the cells in the presence of neuronal media. In certain embodiments the formulation is disposed in vivo in an infarct cavity in a mammalian brain. Also provided is any formulation described herein for use in facilitating recovery from an ischemic event (e.g., a stroke, an acute brain trauma, etc.).

In certain embodiments methods for improving recovery of a mammal after cerebral ischemia are provided where the methods comprise administering an agent to the mammal that enhances AMPA signaling, where the agent is administered after a delay period from the onset of the ischemic event; and where the agent induces an increase in BDNF expression and/or activity. In certain embodiments the agent is not administered until AMPAR signaling switches from promoting cell death to promoting behavioral recovery. In certain embodiments the agent is not administered within the first hour after the onset of the ischemic event. In certain embodiments agent is not administered within the first three hours after the onset of the ischemic event. In certain embodiments the agent is not administered within the first six hours after the onset of the ischemic event, or within the first 12 hours after the onset of the ischemic event, or within the first 24 hours after the onset of the ischemic event. In certain embodiments the agent is administered after at least 24 hours after the onset of the ischemic event, or after at 2 days after the onset of the ischemic event, or after at least 3 days after the onset of the ischemic event, or after at least 4 or 5 days after the onset of the ischemic event, or after at least 7 days after the onset of the ischemic event. In certain embodiments the cerebral ischemia is due to a stroke or a head injury. In certain embodiments the mammal is a human. In certain embodiments the mammal is a non-human mammal. In certain embodiments the agent comprises an ampakine. In certain embodiments the ampakine comprises a high impact (type II) ampakine. In certain embodiments the ampakine is CX1837. In certain embodiments the agent is an agent that crosses the blood/brain barrier. In certain embodiments the agent is delivered directly to the stroke cavity. In certain embodiments the mammal is not diagnosed as having and/or is not under treatment for one or more conditions selected from the group consisting of Alzheimer's disease (AD), attention deficit hyperactivity disorder (ADHD), Parkinson's disease, a sleep disorder, depression, fragile X disorder, mental retardation, and an opiate-induced or other respiratory depression. In certain embodiments the mammal is not diagnosed as having and/or is not under treatment for a neuropsychiatric disorder.

In various embodiments the methods described herein are not used in the treatment of spinal cord injury.

DEFINITIONS

The term "cell line" refers to a mortal or immortal population of cells that is capable of propagation and expansion in vitro.

The term "clonal" refers to a population of cells obtained the expansion of a single cell into a population of cells all derived from that original single cells and not containing other cells.

The term "embryonic stem cells" (ES cells) refers to cells derived from the inner cell mass of blastocysts, blastomeres, or morulae that have been serially passaged as cell lines while maintaining an undifferentiated state (e.g. an undifferentiated state characterized by the expression of one or more markers such as TERT, OCT4, and SSEA and TRA and/or antigens specific for ES cells of the species). In various embodiments the ES cells may be derived from fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, can have a more flattened appearance in culture and may not contribute to germ line differentiation, and are therefore often called "ES-like cells." It is commonly believed that human ES cells are in reality "ES-like", however, as used herein, the term ES cells to refer to both ES and ES-like cells/cell lines.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and U.S. Pat. No. 5,843,780 to Thomson, incorporated herein by reference). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells.

The term "human iPS cells" refers to cells with properties similar to hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; and U.S. Patent Publication 20020142397 (application Ser. No. 10/015,824, entitled "Methods for Altering Cell Fate"); U.S. Patent Publication 20050014258 (application Ser. No. 10/910,156, entitled "Methods for Altering Cell Fate"); U.S. Patent Publication 20030046722 (application Ser. No. 10/032,191, entitled "Methods for cloning mammals using reprogrammed donor chromatin or donor cells"); and U.S. Patent Publication 20060212952 (application Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "pluripotent stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Primordial stem cells may be genetically modified or not genetically modified. Genetically modified cells may include markers such as fluorescent proteins to facilitate their identification in vitro or in vivo.

An "effective amount" or "amount effective to" or "therapeutically effective amount" means a dosage, dosage regimen, or amount sufficient to produce a desired result. In certain embodiments, for example, the desired result can be an increase in BDNF expression, availability, and/or activity.

A "device" means a substance or particle that is injected into the brain and slowly releases the intended molecule, BDNF.

A "hydrogel" (also called aquagel) is a typically crosslinked network of polymer chains (e.g., hyaluronans) that are typically hydrophilic. Hydrogels absorb water and swell. Illustrative examples include, but are not limited to, the hyaluronic acid-based hydrogel, known as HYSTEM® which are crosslinked networks of hyaluronic acid and other thiol-modified macromolecules.

A "nanoparticle" is a particle that has dimensions of less than one micrometer and can be modified to bind or contain other molecules, such as BDNF. In certain embodiments nanoparticles have a characteristic dimension of less than about 750, or less than about 500 nm, or less than about 250 nm. Illustrative nanoparticles include, but are not limited to silica mesoporous nanoparticles or nanoparticles made of major vault protein.

A "low impact ampakine" refers to an ampakine that has little or no effect on the half-width of the field excitatory postsynaptic potential (fEPSP) in electrophysiology studies, does not substantially bind to the cyclothiazide site on the AMPA receptor based upon binding studies and does not induce BDNF expression. Illustrative low impact ampakines include, but are not limited to CX516, CX717, Org24448 and CX1739.

A "high impact ampakine" refers to an refers to an ampakine that substantially alters (increases) the half-width of the field excitatory postsynaptic potential (fEPSP) in electrophysiology studies, and/or substantially bind to the cyclothiazide site on the AMPA receptor based upon binding studies, and induces BDNF expression. Illustrative high impact ampakines include, but are not limited to CX1632 and CX1837.

The terms "drug," "active agent," and "pharmacologically active agent" are used interchangeably herein to refer to any chemical compound, complex or composition that is suitable for oral administration and that has a beneficial biological effect, preferably a therapeutic effect in the treatment of a disease or abnormal physiological condition. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with: (1) the characteristics of the particular drug, including both its pharmacological characteristics and its physical characteristics, such as solubility; (2) the characteristics of the swellable matrix, such as its permeability; and (3) the relative amounts of the drug and polymer. In most cases, the dosage form will be such that effective results will be achieved with administration no more frequently than once every eight hours, preferably no more frequently than once every twelve hours, and even more preferably no more frequently than once every twenty-four hours.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

By an "effective" amount or a "therapeutically effective amount" of a drug or pharmacologically active agent is meant a nontoxic but sufficient amount of the drug or agent to provide the desired effect.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative, refers to a derivative having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well. When the term, "pharmaceutically acceptable" is used to refer to an excipient, it implies that the excipient has met the required standards of toxicological and manufacturing testing or that it is on the Inactive Ingredient Guide prepared by the FDA.

The term "sustained delivery" refers to delivery to the desired site (e.g., infarct cavity) an effective amount of an agent of interest e.g., a growth factor such as BDNF, HBEGF, VEGF, IGF-1, bFGF, and the like, for at least one day, preferably for at least 3 days, at least 4 days, at least 5 days, at least 6 days, more preferably for at least 1 week, at least 2 weeks, at least 3 weeks, or at least 4 weeks, at least 5 weeks, at least 6 weeks, at least 2 months, at least 3 months, or at least 4 months.

A "depot delivery system" refers to a system, device, or formulation that can be placed within the body and that provides a sustained delivery of the active agent(s) of interest e.g., a growth factor such as BDNF, HBEGF, VEGF, IGF-1, bFGF, and the like.

As used herein, the terms "mammal", "subject", and "patient" are used interchangeably. Both human and veterinary applications of the methods and uses of the formulations described herein are contemplated. Accordingly the terms "subject" and "subjects" are used to refer to a non-human mammal (e.g., canine, feline, porcine, ungulate, canine, lagomorph, non-human primate (for example, a monkey, such as a cynomolus monkey, chimpanzee)), or to a human.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

DETAILED DESCRIPTION

Figure 1A:
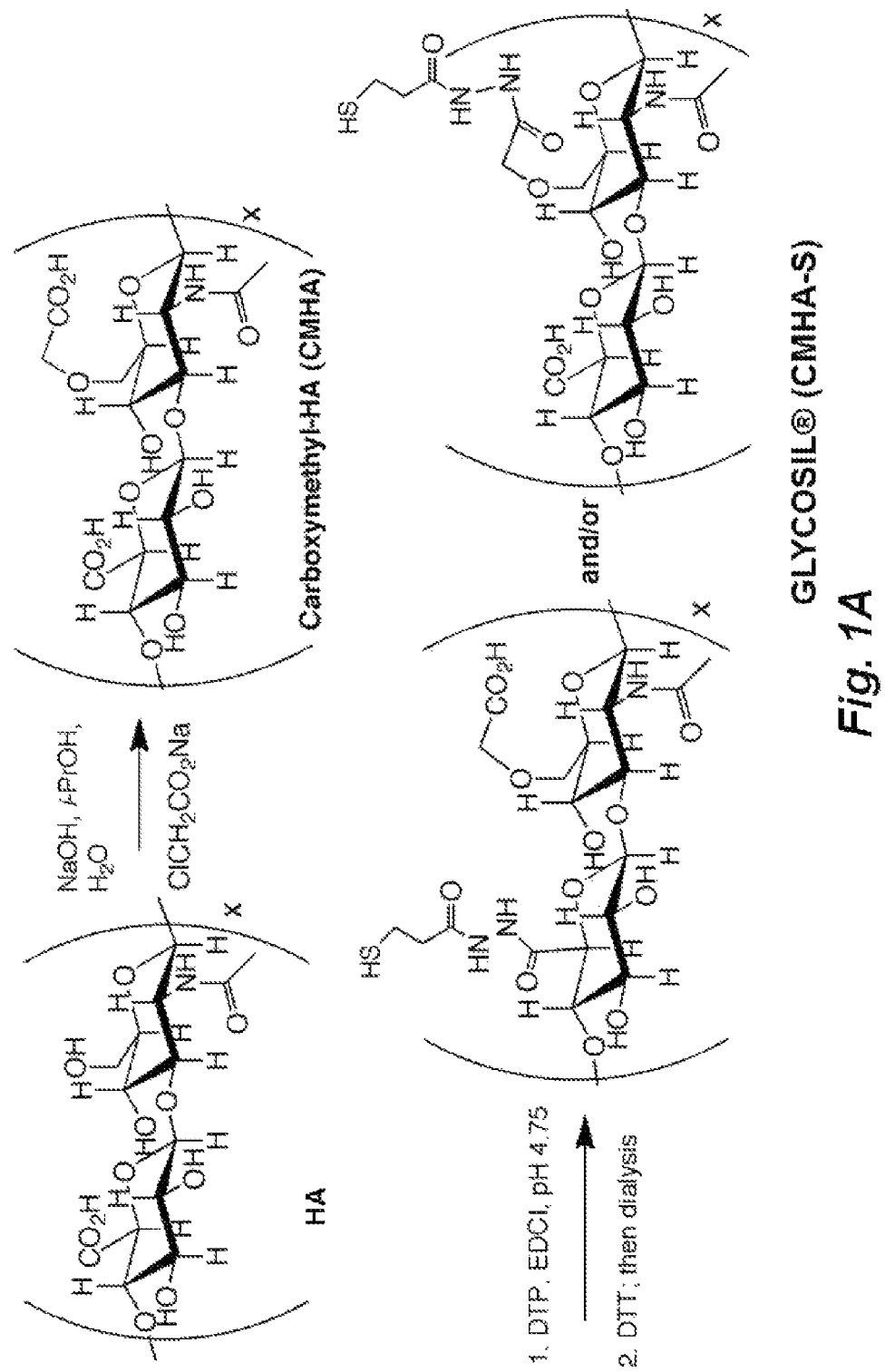
FIGS. 1A and 1B illustrate a process for thiol-modification of hyaluronan (FIG. 1A) and for thiol-modification of gelatin (FIG. 1B) for use in the manufacture of certain hydrogels suitable for the methods described herein.

Methods are provided herein that produce improved recovery in stroke or other cerebral ischemic conditions. In certain embodiments the methods involve slowly releasing a brain growth factor from a medical device (or implantable depot pharmaceutical formulation) in or into the ischemic (e.g., stroke) cavity. It was a surprising discovery that slow (controlled/sustained) release of a brain growth factor, such as BNDF, into the ischemic cavity can substantially and dramatically improve the rate and/or degree of recovery after the ischemic event. In various embodiments, the methods involve depositing slow/sustained release delivery vehicle comprising one or more brain growth factors and/or cells that express/secrete one or more brain growth factors into the ischemic (e.g., stroke) cavity (the area of cell death and absorption of dead tissue) in the brain subject to the ischemic event. The tissue adjacent to the stroke cavity undergoes the most substantial recovery of function after ischemia. This recovering brain tissue is termed the periinfarct tissue.

Without being bound to a particular theory, it is believed that AMPAR function plays a critical but functionally contradictory role in the spectrum of stroke pathophysiology. AMPAR signaling in the tissue adjacent to the infarct mediates behavioral recovery of limb control over weeks after the stroke. This process occurs through BDNF induction in periinfarct cortex. Positive AMPAR modulation in a way that also induces BDNF promotes improved recovery of motor function during this recovery phase after stroke and blockade of AMPA signaling retards motor recovery. However, immediately after stroke, AMPARs are involved in cell death and infarct evolution. Positive AMPAR modulation increases infarct size immediately after stroke. These data indicate that there is an inflection point within the first several days after stroke where AMPAR signaling switches from promoting cell death to promoting behavioral recovery. Positive modulation of AMPAR signaling during stroke recovery is a novel pharmacological target to promote improved behavioral outcomes in this disease.

More particularly without being bound to a theory we believe that AMPAR signaling after stroke controls major aspects of motor recovery via an increase in local BDNF levels.

Data presented herein show a clear role for BDNF signaling in behavioral recovery after stroke. Systemic administration of CX1837 induces BDNF levels and TrkB phosphorylation in periinfarct cortex. Local blockade of BDNF induction in periinfarct cortex not only prevents the ampakine-mediated behavioral recovery but also generally blocks motor recovery after stroke. The present data indicate that BDNF normally mediates motor recovery after stroke, localizes this effect to the periinfarct cortex adjacent to the stroke site, and identifies a systemic pharmacological therapy that will modulate BDNF in this critical periinfarct region for motor recovery. It is believed these data are the first to specifically localize motor recovery to one brain region after stroke, the periinfarct cortex.

While data presented herein relate primarily to the administration of BDNF it is believed that administration of other brain growth factors and/or cells secreting other brain growth factors can provide similar benefits.

Because BDNF and other neural (brain) growth factors do not easily pass the blood brain barrier and are likely to have significant toxicity if given systemically, in various embodiments, local administration into the infarct cavity (stroke cavity) is contemplated. Moreover, in various embodiments certain depot delivery systems, in particular hydrogel depot formulations show surprising efficacy along with an effective sustained release profile. Accordingly, in various embodiments, methods of improving recovery of a mammal after cerebral ischemia are provided where the method comprises administering a therapeutically effective amount of a brain growth factor to the infarct cavity in the brain of mammal. In certain embodiments, the administering comprises depositing a depot delivery system into the infarct cavity where the depot delivery system comprises/contains the growth factor(s) and provides sustained release of the growth factor(s) over time, and/or the depot delivery system comprises cells that provide a sustained release of the brain growth factor. In various embodiments the depot delivery system comprises a hydrogel.

Depot Delivery Systems.

In various embodiments the methods described herein contemplate the introduction of one or more depot delivery systems into the infarct cavity where they provide a sustained release of neural (brain) growth factors (e.g., BDNF, HBEGF, VEGF, IGF-1, bFGF, and the like) as described herein. In certain embodiments the depot delivery systems comprise one or more growth factors and provide a sustained release of those growth factors and/or they comprise cells that provide a sustained release of one or more growth factors.

Implantable sustained delivery systems are known to those of skill in the art. Such systems include, but are not limited to, mechanical and/or electronic devices such as implantable drug pumps or microchip systems as well as implantable controlled delivery polymeric matrices.

Implantable microchip systems, include systems such as the MICROCHIPS® device (MicroChips, Inc. Bedford Mass.). The MicroCHIPS implantable drug delivery system (IDDS) is based on a microfabricated silicon chip that contains multiple drug-filled reservoirs. the chip is attached to a titanium case containing a battery, control circuitry, and telemetry. The drug chip and titanium case are hermetically sealed and electrically linked by a ceramic substrate with metal interconnects. The IDDS communicates with an external handheld controller through wireless transmission. A drug regimen can be transmitted to the implanted device through this link, allowing reservoirs to be opened at prescribed times without any need for further communication. Alternatively, reservoirs can be opened as desired on command from the controller.

Controlled release polymeric devices can be made for long term release following implantation. Illustrative controlled polymeric release devices comprise an implantable rod, cylinder, film, disk, and the like, or an injectable polymeric formulation (e.g. a microparticle formulation). In various embodiments the implantable matrix can be in the form of microparticles such as microspheres, where the brain growth factor(s) (e.g., BNDF) are dispersed within a solid polymeric matrix or microcapsules. Typically in such systems the core is of a different material than the polymeric shell, and the active agent (e.g., BNDF) will be dispersed or suspended in the core, which may be liquid or solid in nature. Alternatively, the polymer may be cast as a thin slab or film, ranging from, e.g., nanometers to four centimeters, a powder produced by grinding or other standard techniques, or may be suspended in the soluble components of a hydrogel prior to crosslinking.

In certain embodiments either non-biodegradable or biodegradable matrices can be used for delivery of brain growth factors and/or cells as described herein, however, biodegradable matrices are typically preferred. These can include natural or synthetic polymers. Often synthetic polymers provide better characterization of degradation and release profiles. The polymer is typically selected based on the period over which release is desired. In some cases linear release may be most useful, although in others a pulse release or "bulk release" may provide more effective results. As discussed below, in certain embodiments, the polymer is in the form of a hydrogel, and can optionally be crosslinked with multivalent ions or polymers.

In various embodiments the matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer (1987) *J. Controlled Release* 5:13-22; Mathiowitz, et al. (1987) *Reactive Polymers* 6: 275-283, Mathiowitz, et al. (1988) *J. Appl. Polymer Sci.* 35:755-774, and the like.

In various embodiments the devices can be formulated for local release to treat the area of implantation, e.g., the infarct cavity. In various embodiments these can be implanted or injected into the desired region.

In certain embodiments the implantable the depot delivery systems comprise a microparticles patterned within a hydrogel. In one illustrative embodiment, the growth factors are provided within microparticles (e.g., PLGA microparticles) entrapped within a hydrogel (e.g., PEG hydrogel) base. Such systems have been constructed to deliver agents with two different delivery profiles (see, e.g., Wang et al. (2011) Pharmaceutical Res., 28(6): 1406-1414).

In various embodiments the methods provided herein utilize a hydrogel, preferably a biopolymer hydrogel to contain and provide sustained release of the growth factor(s) (e.g., BDNF, and/or other neural tissue growth factors) into the infarct cavity and/or to contain cells (e.g., stem cells) that afford sustained release of one or more brain growth factors). In certain embodiments the hydrogel can be made of naturally occurring brain proteins, and does not provoke a brain reaction. In some embodiments, the hydrogel can be a HYSTEM® hydrogel (e.g., a HYSTEM®-C hydrogel, a HYSTEM®-HP hydrogel, and the like).

In various embodiments the growth factor(s) are released slowly over at least one day, or over at least 3 days or over at least 5 days, or over at least one week, or over at least two weeks, or over at least 3 weeks, or over at least one month, or over at least two months, or over at least three months, or over at least six months. Typically the growth factor(s) are released directly to the target tissue in the body (e.g., the peri-infarct issue) after the ischemic event (e.g., stroke) and produce an improvement in recovery from the ischemic event.

The use of a hydrogel to contain one or more growth factors and/or cells that secrete one or more brain growth factors and to deliver these growth factor(s) in a sustained manner directly to the area of repair and recovery in the brain (e.g., the infarct cavity) is believed to offer a number of advantages. First, the delivery is locally done within the brain. Systemic delivery of a growth factor after stroke, such as intravenous, intra-arterial or oral delivery, exposes the whole body to the growth factor. BDNF and other growth factors are "pleiotropic". They have many actions on other organ systems in the body besides the brain. This pleiotropic action means that giving a growth factor systemically will cause untoward effects outside of the brain. These systemic effects caused the only clinical trial of a growth factor for stroke to fail, bFGF (Ren and Finklestein (2005) *Curr. Drug Targets CNS Neurol. Disord.* 4: 121-125). Systemic effects caused the failure of a cytokine that is related to growth factors, erythropoietin, to also fail in stroke (Ehrenreich et al. (2009) *Stroke* 40: e647-e656).

Hydrogel delivery of BDNF (or other growth factors) and/or hydrogel containment of cells that secrete growth factors from the stroke cavity bypasses the blood brain barrier. The blood brain barrier blocks delivery of most growth factors from the systemic circulation to the brain (Wu (2005) *NeuroRx* 2: 120-128). In various embodiments the hydrogel systems contemplated herein provide sustained release of the growth factor(s). In various embodiments the release of the growth factors (e.g., BDNF, HBEGF, VEGF, IGF-1, bFGF, and the like) from the hydrogel occurs for one month or longer after just one delivery. The growth factor containing and/or cell containing hydrogel is delivered into the infarct cavity and slowly releases the growth factor (e.g., BDNF). Other delivery methods that also bypass the blood brain barrier and produce direct growth factor delivery to the brain use viral gene transfer (Wang et al. (2006) *Front Biosci.* 11: 1101-1107). With current technology, viral gene transfer cannot be turned off, meaning that the growth factor will be continuously produced for the life of the patient. This continuous production of growth factor is associated with potential side effects, including tumor formation (Ruitenberg et al. (2002) *Methods* 28: 182-194; Blomer et al (2002) *Adv. Exp. Med. Bid.,* 513: 431-451). Hydrogel delivery of growth factors as described herein can utilize a hydrogel that is made of naturally occurring brain components, including proteins and glycosaminoglycans such as hyaluronic acid or its derivatives, and does not promote inflammation or tissue damage (Zhong et al. (2010) *Neurorehabil. Neural. Repair,* 24:636). In various embodiments the hydrogels contemplated herein are designed to crosslink into the hydrogel form starting from a liquid form after it is injected into the brain. Other hydrogels or tissue engineering approaches use semi-rigid substances that must be implanted. The liquid and delayed self-assembly of these hydrogels and the surprising discovery that they permit injection without shearing forces that would destroy cells allows a very small needle delivery into the brain.

In certain embodiments the use of hyaluronan based hydrogels is contemplated and preferred. A family of well suited hydrogels is produced by BioTime and are marketed under the name HYSTEM®. In certain embodiments the hydrogels mimic the natural extracellular matrix environment (ECM) and are designed to recapitulate the minimal composition necessary to obtain a functional ECM.

In various embodiments the individual components of the hydrogels are cross-linkable in situ, and can be seeded with the brain growth factors (e.g., BDNF, HBEGF, VEGF, IGF-1, bFGF, and the like) or cells prior to injection in vivo, without compromising either the cells or the recipient tissues.

In certain embodiments the hydrogel comprises a hyaluronan (or a functionalized/derivatized hyaluronan) and a gelatin (or a functionalized/derivatized gelatin). In various embodiments the hyaluronan and/or the gelatin are each thiol-modified, e.g., by using carbodiimide mediated hydrazide chemistry. In some embodiments, the gel-forming material is based on chemically-modified hyaluronic acid. In some embodiments, the gel-forming hyaluronic acid matrix is HYSTEM®, HYSTEM®-HP, or HYSTEM®-C. The HYSTEM® hydrogels are formed by crosslinking mixtures of these thiolated macromolecules using polyethylene glycol diacrylate (PEGDA) or other suitable cross-linkers. The rate of gelation and hydrogel stiffness can be controlled by varying the amount of cross-linker. In certain embodiments an important attribute of the hydrogels used herein (e.g., HYSTEM® hydrogels) is their large water content, typically greater than about 95% resulting in high permeability for oxygen, nutrients, and other water-soluble metabolites.

The co-crosslinked hyaluronan/gelatin hydrogels contemplated for use in certain embodiments described herein have been shown to support attachment and proliferation of a wide variety of cell types in both 2-D and 3-D cultures and exhibit a high degree of biocompatibility when implanted in vivo. These hydrogels are readily resorbed in vitro and in vivo through hydrolysis by collagenase, chondroitinase and hyaluronidase enzymes. When implanted in HYSTEM® hydrogels, cells remain attached and localized within the hydrogel and slowly degrade the implanted matrix replacing it with their natural ECMs.

In various embodiments the hydrogels are initially provided as a three component system comprising 1) a hyaluronan (e.g., a thiol-modified hyaluronan), 2) a gelatin (e.g., a thiol-modified gelatin; and 3) a linker (e.g., a polyethyleneglycoldiacrylate linker). In one commercially available system, the HYSTEM®-C system these are provided as the three components: GLYCOSIL® (thiol-modified hyaluronan), GELIN®-S (thiol-modified gelatin) and EXTRALINK® (polyethyleneglycol diacrylate). The individual components are supplied in vials as pre-measured, sterile, lyophilized solids that, when dissolved in physiologic buffer (i.e. normal saline, Lactated Ringers, etc.) and mixed together, form a clear, transparent viscoelastic hydrogel in approximately 20 minutes at room temperature. The compliance (stiffness) of the hydrogel is ~70+20 Pa which is similar to adipose and neural tissue. The lyophilized hydrogel components contain no extra salts so that upon dissolution in physiologic buffer the resultant gel is isotonic with a pH ~7.4. In certain embodiments the typical percent solids of a suitable hydrogel (e.g., HYSTEM®-C hydrogel is less than 2.0% (w/v) and the EXTRALINK® cross-linker concentration utilizes less than 30% of the available thiol groups on the other components so that any unreacted acrylate groups of the cross-linker are negligible. Typically, one ml of HYSTEM®-C hydrogel formulated in physiologic buffer contains 4 mg of GLYCOSIL® and 4 mg of GELIN® cross-linked with 4 mg of EXTRALINK® at the ionic strength and pH of the formulation buffer. In certain embodiments for in vivo applications in, typical hydrogel volumes may range between 0.1, or 0.5, or 1.0 ml/implant site up to 5.0 ml, 4.0 ml, or 3.0 ml, or 2.0 ml per implant site with a total volume of up to 20 mls, 15 mls, or 10 mls of hydrogel in situations with multiple implant sites per tissue or organ.

Methods of making the thiol-modified macromolecules are known in the art. In one approach, dithiobispropanoic dihydrazide (DTP) is coupled to the carboxyl functional groups of the macromolecule by reaction with N-(3-dimethylaminopropyl)-N'-ethylcarbodiimide hydrochloride (EDC) followed by reductive cleavage of the DTP disulfide bonds with dithiothreitol (DTT) to yield the thiol-modified macromolecule DTPH derivatives. The thiol-modified products are purified by exhaustive tangential flow filtration (TFF) using a polyethersulfone membrane with a 10 kDa lower exclusion limit. Since the reagents and reaction byproducts are all small molecules, this latter step produces very high purity thiol-modified macromolecules. For GLYCOSIL®, the hyaluronan component of HYSTEM®-C, prior to thiol modification the molecular weight of the polymer is normalized by controlled basic hydrolysis and the available carbonyl functional groups are increased by carboxymethylation of the 6' hydroxyl of the glucosamine moiety of the polymer with chloroacetic acid in strong base. Gelatin is thiol-modified as supplied without any pretreatment, and the product is called GELIN®-S.

Figure 1B:
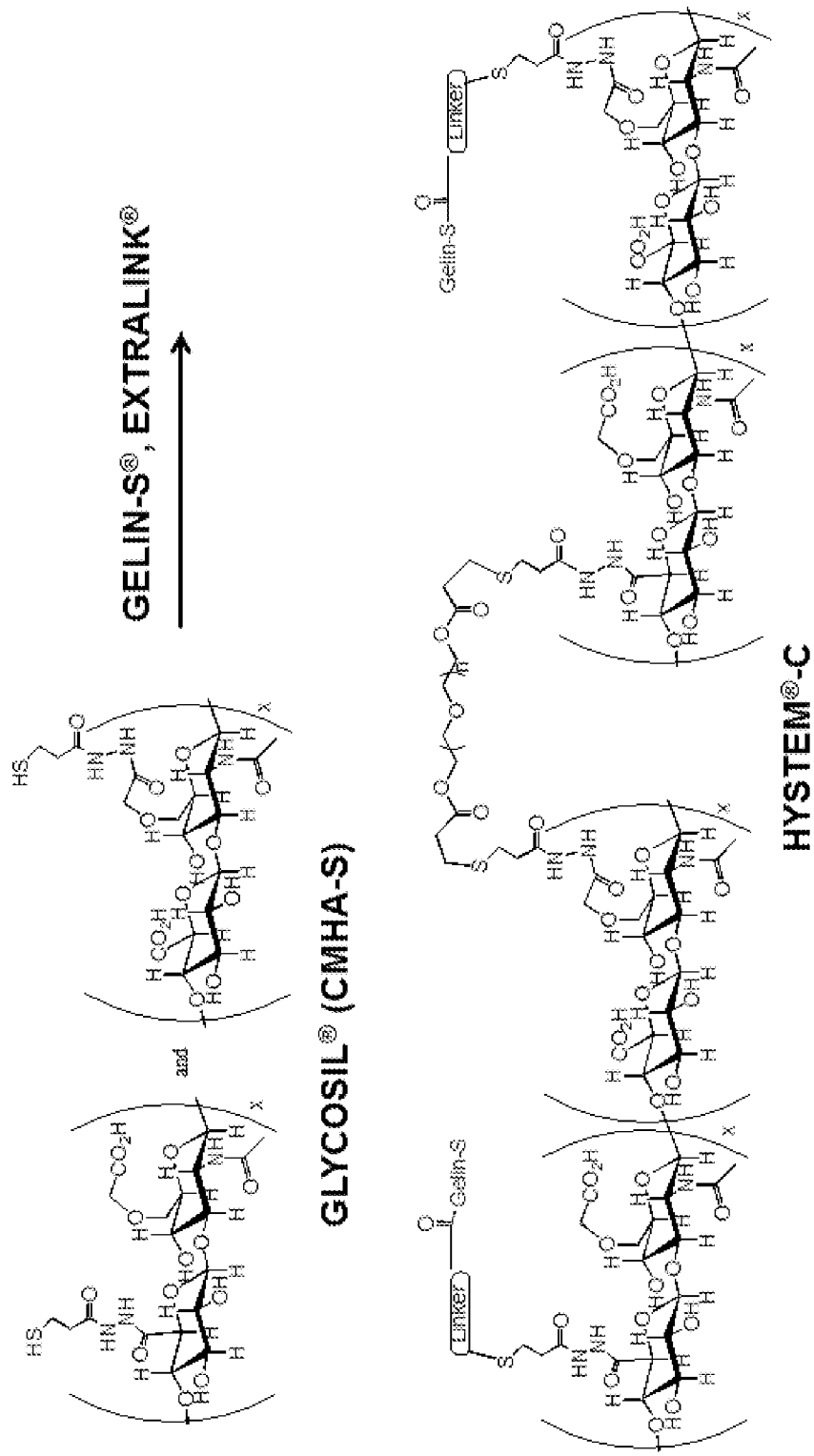

These reactions are illustrated in FIGS. 1A and 1B. FIG. 1A illustrates the preparation of thiol-modified hyaluronan from hyaluronan (HA). The chemical modification of HA to produce carboxymethyl HA (CMHA) occurs in basic solution and modifies approximately 15-20% of the 6'-OH groups of the N-acetylglucosamine residues, as determined by proton NMR. This process reduces the molecular weight and introduces additional carboxyl groups for subsequent thiol-modification and creates the novel molecular scaffold.

The second step is the conversion of carboxyl groups to thiol functionalities. With thiol-modified hyaluronan this occurs preferentially at the newly added carboxymethyl carboxylic acid groups, and next at a fraction of the glucuronic acid carboxylic acid moieties of the HA backbone. As a result, the thiol-modified hyaluronan (e.g., GLYCOSIL®) has most of its thiol groups for cross-linking on the newly introduced carboxymethyl groups, which preserves the structure of the hyaluronan backbone and allows better recognition of HA by cellular proteins. The preparation of thiol-modified gelatin and thiol-modified hyaluronan is described in U.S. Pat. Nos. 7,928,069 and 7,981,871.

In HYSTEM®-C, GELIN®-S (thiol modified gelatin) is mixed with GLYCOSIL® (CMHA-S) prior to cross-linking with EXTRALINK®. Thiol-modified gelatin can be prepared from porcine gelatin by the same thiol-modification chemistry as used for hyaluronan. The reaction sequence for producing a HYSTEM®-C hydrogel is illustrated in FIG. 1B.

In certain embodiments the hydrogel used to contain the growth factor(s) and/or the cells that release growth factors comprises a heparin. In certain embodiments the hydrogel comprises chemical derivatives of hyaluronan, gelatin and heparin. One illustrative commercially available formulation of such a hydrogel is HYSTEM®-HP. HYSTEM®-HP contains small amounts of thiolated heparin that can ionically bind a wide variety of growth factors and slowly releases them over time.

HYSTEM®-HP hydrogels contains thiol-modified heparin which allows the slow release of growth factors (GFs) within an easily customizable, environment. In certain embodiments, the hydrogel is just formulated with a thiolated hyaluronan and a thiolated heparin. This hydrogel is a synthetic extracellular matrix (ECM) that can be injected and crosslinked in situ. Unlike an animal-derived extracellular matrix (ECM), HYSTEM®-HP is chemically defined and is typically nonimmunogenic. In certain embodiments the hydrogel is formulated with a thiolated hyaluronan, a thiolated heparin, and a thiolated gelatin. In various embodiments the immobilized heparin in the hydrogel mimics the heparin sulfate proteoglycans normally present in the extracellular matrix (ECM). It also helps protect growth factors from proteolysis and slows their release to attached cells. This reduces the amount of growth factor required to achieve stimulation of cell growth or differentiation when compared to the use of free growth factor in media.

The thiol-modified hyaluronate hydrogels, such as the HYSTEM® products described herein, have demonstrated broad biocompatibility among a variety of cell types. Moreover, in vivo studies of cells encapsulated such hydrogels show excellent compatibility in the host animal without evidence of inflammation or immune response arising from the implanted hydrogel.

Another example of a crosslinked hydrogel comprises thiol-modified hyaluronan and thiol-modified heparin reacted with a thiol-reactive crosslinker such as polyethylene glycol diacrylate. Examples also include hyaluronan sodium salt solution mixed with ADH and carbodiimide reagent (EDC); or acrylated hyaluronic acid dissolved in a TEA-buffered solution and mixed cross-linker peptides such as GCRDGPQGIWGQDRCG (SEQ ID NO:1), or GCRDGDQGIAGFDRCG (SEQ ID NO:2), and the like. The growth factor(s) (e.g., BDNF) are added to the hydrogel solution, for example at 100 µg/mL of solution. The gel/growth factor (e.g., BDNF) mixture is injected into the ischemic (stroke) cavity based on stereotaxic coordinates identified for the stroke.

Other illustrative and non-limiting hydrogels include, for example, calcium crosslinked alginate, photocrosslinked alginate, and collagen hydrogels (see, e.g., Krebs et al. (2009) *J. Am. Chem. Soc.*, 131(26): 9204-9206). Gils, et al. (2010 *Am. J. Biomed. Sci.* 2(4), 373-383 describe modification of xanthum gum (XG) polysaccharide to produce drug delivery hydrogels. In particular, they prepared XG-g-poly [HEMA-co-AA] superporous hydrogel (SPH) through chemical cross-linking by graft copolymerization of 2-hydroxyethyl methacrylate (HEMA) and acrylic acid (AA) on to XG via redox initiator system of ammonium persulfate (APS) and N, N, N',N'-tetramethylethylenediamine (TMED), in the presence of N,N'-methylenebisacrylamide (MBA) crosslinking agent, sodium bicarbonate foaming agent, a triblock copolymer of polyoxyethylene/polyoxypropylene/polyoxyethylene as a foam stabilizer. Oxidized alginate and gelatin (e.g., periodate oxidized sodium alginate) hydrogels are described by Balakrishnan and Jayakrishnan (2005) *Biomaterials* 26(18): 3941-3951. A number of injectable hydrogel systems (alginate, chitosan, hyaluronan, polyethylene oxide/polypropylene oxide) are described by Gutowska et al. (2001) *Anat Rec.* 263(4): 342-349. A dextran-aldehyde conjugate hydrogel can be formulated by mixing carboxymethylcellulose-hydrazide with dextran-aldehyde (see, e.g., Hudson et al. (2010) *Biomaterials* 31(6): 1444-1452). In addition, CM-Tec (Newark, Del.) offers commercial hydrogels made from gelatin and polyaspartate (or polyglutamate).

These formulations and protocols are intended to be illustrative and non-limiting. Using the teachings provided herein, other suitable hydrogel formulations will be available to one of skill in the art.

Brain Growth Factors.

As indicated above, the methods described herein contemplate deliver of brain growth factors (e.g., BDNF, HBEGF, VEGF, IGF-1, bFGF, and the like) to the infarct cavity to improve recovery from an ischemic event. In certain embodiments the growth factors are contained in a hydrogel (or other sustained delivery system) delivered to the infarct cavity. In certain embodiments growth factors are secreted by cells contained within a hydrogel or other delivery system delivered to the infarct cavity. In certain embodiments the growth factors provided in the delivery system and/or the growth factors secreted by the cells comprise one or more of the brain growth factors listed in Table 1.

TABLE 1

Illustrative, but non-limiting list of growth factors for use in the methods described herein.

| | |
|---|---|
| Ang1 | angiopoietin 1 |
| Ang 2 | angiopoietin 2 |
| BDNF | brain derived neurotrophic factor |
| BMP 2 | bone morphogenic protein 2 |

TABLE 1-continued

Illustrative, but non-limiting list of growth factors for use in the methods described herein.

| | |
|---|---|
| BMP 3a | bone morphogenic protein 3a |
| BMP 3b | bone morphogenic protein 3b |
| BMP 4 | bone morphogenic protein 4 |
| BMP 5 | bone morphogenic protein 5 |
| BMP 6 | bone morphogenic protein 6 |
| BMP 7 (OP-1) | bone morphogenic protein 7 (osteogenic protein 1) |
| CTNF | ciliary neurotrophic factor |
| EGF | epidermal growth factor |
| EPO | erythropoetin |
| aFGF/FGF1 | acidic fibroblast growth factor |
| bFGF/FGF2 | basic fibroblast growth factor |
| G-CSF | granulocyte colony stimulating factor |
| GDF10 | growth differentiation factor 10 |
| GDF15 | growth differentiation factor 15 |
| GDNF | glial derived neurotrophic factor |
| GH | growth hormone |
| GM-CSF | granulocyte moncoyte colony stimulating factor |
| HB-EGF | heparin binding epidermal growth factor |
| IGF1 | insulin like growth factor 1 |
| LIF | leukemia inhibitory factor |
| NGF | nerve growth factor |
| NT-3 | neurotrophin 3 |
| NT 4/5 | neurotrophin 4/5 (same molecule) |
| Osteopontin | |
| PDGFaa | platelet derived growth factor with a/a subunit composition |
| PDGFbb | platelet derived growth factor with b/b subunit composition |
| PDGFab | platelet derived growth factor with a/b subunit composition |
| PlGF | placental growth factor |
| SCF | stem cell factor |
| SDF1/CXCL12 | stromal derived factor 1 |
| TGFβ | transforming growth factor beta |
| VEGF | vascular endothelial growth factor |

In certain embodiments a single growth factor (e.g., BDNF, or HBEGF, or VEGF, or IGF-1, or bFGF, and the like) is provided in the hydrogel and/or secreted by the cell(s). In certain embodiments two growth factors or three growth factors, or 4 growth factors, or 5 growth factors, or 6 growth factors, or 7 growth factors, or 8 growth factors, or 9 growth factors, independently selected from Table 1 are contemplated.

Use of Cells as a Source of BDNF and Other Factors Useful in Improving Recovery from Stroke.

In various embodiments the method described herein contemplate the use of cells (e.g., stem cells or other progenitor cells) as a source of BDNF and/or the other factors for use in the methods described herein. In certain embodiments the cells are provided in the delivery system (e.g., a hydrogel) that is introduced into the infarct cavity where they provided a source for sustained release of the desired growth factors. In certain embodiments the cells include stem cells (e.g., adult stem cells, embryonic stem cells, cord stem cells, induced pluripotent stem cells (IP-SCs), and the like). In certain embodiments the cells are cells that have differentiated from stem cells in culture or after implantation into said mammal.

In various embodiments the cells comprise clonal human embryonic progenitor cell lines and can act as a source of BDNF and other growth factors useful in improving recovery from stroke.

Methods of obtaining such cells are known to those of skill in the art. In particular, methods that find use in the production and use of the clonal, oligoclonal, or pooled clonal or pooled oligoclonal cell lines producing factors useful in improving recovery from stroke described herein can be found in the following: U.S. Patent Publication Nos:

2008/0070303, 2010/0184033, U.S. provisional application Ser. No. 61/226,237 filed on Jul. 16, 2009 and titled "Methods and Compositions Useful for In Vitro and In Vivo Chondrogenesis Using Embryonic Progenitor Cell Lines"; PCT Application No: PCT/US2006/013519 and PCT Application No: PCT/US2011/037969, each of which is incorporated by reference herein in its entirety.

By way of illustration, human ES-derived clonal, oligoclonal, or pooled clonal or pooled oligoclonal embryonic progenitor cell lines that express BDNF, HBEGF, VEGF, IGF-1, or bFGF, or combinations of these factors, may be introduced into the stroke cavity or peri-infarct region of the stroke as a means of continuous delivery of these factors to facilitate recovery. These cells may be in a normal state previously propagated in vitro, or alternatively, they may be mitotically inactivated to limit the risk of undesired proliferation as is well-known in the art such as by treatment with mitomycin-C. The transplantation of these cells and slow release of the factors may be facilitated by transplantation of the cells into the stroke cavity or peri-infarct region with hydrogel matrices including, but not limited to HYSTEM®, and/or HYSTEM®-C, and/or HYSTEM®-HP-C as described herein.

Alternatively, human ES-derived Clonal, oligoclonal, or pooled clonal or pooled oligoclonal embryonic progenitor cell lines that express growth factors such as BDNF, HBEGF, VEGF (e.g., VEGFA), IGF-1, bFGF, and the like, or combinations of these factors, may be cultured in vitro to obtain secreted proteins that are in turn formulated with slow release hydrogels such as HYSTEM®-C as described herein. Such preparations of secreted proteins from the embryonic progenitor cell lines may be accomplished by many means known in the art including the collection of conditioned medium and the fractionation or concentration of the protein components of said media. Additional examples that may be used for the preparation of various secreted proteins are as follows:

Secreted Protein Isolation Protocol 1: Isolation of Secreted or Extracellular Matrix Proteins Cells are grown in either their normal propagation medium (West et al. (2008) *Regen Med.,* 3(3): 287-308) or the differentiation conditions described herein. To obtain conditioned medium on a smaller scale (typically 1-2 L or less), the cells are grown in monolayer cultures in T150, T175 or T225 flasks (Corning or BD Falcon) in a 37° C. incubator with 10% $CO_2$ atmosphere. For larger volume medium collections, the cells are typically grown either in 2 L roller bottles, on microcarrier suspensions (porous such as Cytodex varieties from Sigma-Aldrich, St. Louis, Mo., or non-porous such as from SoloHill Engineering, Ann Arbor, Mich.) in spinner flasks or other bioreactors, or in hollow fiber cartridge bioreactors (GE Healthcare, Piscataway, N.J.). Prior to conditioned medium collection, the cultures are rinsed twice with PBS and then incubated for 2 hours at 37° C. in the presence of serum-free medium wherein the medium is the same basal medium as described herein for the propagation or differentiation of the cells, in order to remove fetal serum proteins. The serum-free medium is then removed and replaced with fresh medium, followed by continued as described herein at 37° C. for 24-48 hours.

The culture-conditioned medium is then collected by separation from the cell-bound vessel surface or matrix (e.g., by pouring off directly or after sedimentation) and processed further for secreted protein concentration, enrichment or purification. As deemed appropriate for the collection volume, the culture medium is first centrifuged at 500 to 10,000×g to remove residual cells and cellular debris in 15 or 50 ml centrifuge tubes or 250 ml bottles. It is then passaged through successive 1 µm or 0.45 µm and 0.2 µm filter units (Corning) to remove additional debris, and then concentrated using 10,000 MW cutoff ultrafiltration in a stirred cell or Centricon centrifuge filter (Amicon-Millipore) for smaller volumes, or using a tangential flow ultrafiltration unit (Amicon-Millipore) for larger volumes. The retained protein concentrate is then dialyzed into an appropriate buffer for subsequent purification of specific proteins, and further purified using a combination of isoelectric focusing, size exclusion chromatography, ion exchange chromatography, hydrophobic or reverse phase chromatography, antibody affinity chromatography or other well-known methods appropriate for the specific proteins. During the various steps in the purification process, collection fractions are tested for the presence and quantity of the specific secreted protein by ELISA (e.g., using BMP-2 or BMP-7 ELISA kits from R&D Systems, Minneapolis, Minn.). The purified proteins are then kept in solution or lyophilized and then stored at 4° C. or minus 20-80° C.

Secreted Protein Isolation Protocol 2—Urea-Mediated Protein Extraction

In the case of some secreted proteins, interactions with the cell or ECM components may reduce the simple diffusion of factors into the medium as described above in Secreted Protein Isolation Protocol 1. A simple comparison of the yield in the two protocols will suffice to determine which protocol provides the highest yield of the desired factors. In the case of Secreted Protein Isolation Protocol 2, a low concentration of urea is added to facilitate the removal of factors. In the case of the examples provided, all urea extractions are performed two days subsequent to feeding. On the second day, cell monolayers in T-150 cell culture flasks are rinsed twice with CMF-PBS and then incubated for two hours at 37° C. in the presence of serum-free medium. The rinse with CMF-PBS and the incubation in serum-free medium together aid in the removal of fetal serum proteins from the surface of the cells. The serum-free medium is then removed and 10 ml/T150 of freshly made 200 mM urea in CMF-PBS was added. The flasks are then placed on a rocker at 37° C. for 6.0 hours. The urea solution was then removed and immediately frozen at −70° C.

Extracellular Matrix Isolation Protocol 1—DOC-Mediated Preparation

Extracellular matrix proteins can be extracted using the method of Hedman et al. (1979) *J. Cell Biol.* 81: 83-91. Cell layers are rinsed three times with CMF-PBS buffer at ambient temperature and then washed with 30 mL of 0.5% sodium deoxycholate (DOC), 1 mM phenylmethylsulfonylfluride (PMSF, from 0.4M solution in EtOH), CMF-PBS buffer 3×10 min. on ice while on a rocking platform. The flasks are then washed in the same manner with 2 mM Tris-HCl, pH 8.0 and 1 mM PMSF 3×5 min. The protein remaining attached to the flask is then removed in 2 mL of gel loading buffer with a rubber policeman.

Screening of Secreted or Extracellular Matrix Proteins for Biological Activity

The cell lines described herein are also useful as a means of screening diverse embryonic secretomes for varied biological activities. The cell lines of the present invention cultured at 18-21 doublings of clonal expansion express a wide array of secreted soluble and extracellular matrix genes (see US Patent Application Publication 2010/0184033, incorporated herein by reference). At 21 or more doublings of clonal expansion, the cells of the present invention differentially express secreted soluble and extracellular matrix genes. These proteins, proteoglycans, cytokines, and growth factors may be harvested from the cell lines of the present invention by various techniques known in the art including but not limited to Secreted Protein Isolation Protocol 1 or 2. These pools of secreted and extracellular matrix proteins may be further purified or used as mixtures of factors and used in varied in vitro or in vivo assays of biological activity as is known in the art.

Clonal embryonic progenitor cell lines useful in the production of BDNF include, but are not limited to, SM22, CM02, E33, 7PEND24, B16, C4ELS5.1, T36, E68, T43, W10, and EN13. BDNF expression was enhanced by culturing the cells in the presence of neuronal media such as neurobasal medium (Cat. No. 12348-017) with N2 purchased from Invitrogen. DMEM (Cat. No. 11960-069) or B27, and the like.

Clonal embryonic progenitor cell lines useful in the production of HBEGF include, but are not limited to SM22, CM02, E33, and EN13, and the like.

Clonal embryonic progenitor cell lines useful in the production of VEGFA include, but are not limited to SM22, CM02, E33, and EN13, and the like.

Clonal embryonic progenitor cell lines useful in the production of IGF1 include, but are not limited to include: SM22, CM02, and EN13, and the like.

Clonal embryonic progenitor cell lines useful in the production of bFGF include, but are not limited to SM22, CM02, E33, and EN13, and the like.

The molecular markers of the cell lines SM22, CM02, E33, 7PEND24, B16, C4ELS5.1, T36, E68, T43, W10, and EN13 from 18-21 doublings from the initial clonal expansion from hES cells can be found in the following: U.S. Patent Publication 2008/0070303; 2010/0184033 A1; U.S. provisional application Ser. No. 61/226,237 filed on Jul. 16, 2009 and titled "Methods and Compositions Useful for In Vitro and In Vivo Chondrogenesis Using Embryonic Progenitor Cell Lines"; PCT Application No: PCT/US2006/013519 and PCT Application No: PCT/US2011/037969, each of which is incorporated by reference herein in its entirety. In brief, the gene expression markers for the cell line 7PEND24 are: AQP1, BEX1, CDH3, DIO2, DLK1, FOXF1, FST, GABRB1, IGF2, IGFBP5, IL1R1, KIAA0644, MSX1, PODN, PRRX2, SERPINA3, SOX11, SRCRB4D and TFPI2 and are negative for the markers: ACTC, AGC1, AKR1C1, ALDH1A1, ANXA8, APCDD1, AREG, CFB, C3, C6, C7, PRSS35, CCDC3, CD24, CLDN11, COMP, COP1, CXADR, DKK2, EMID1, FGFR3, FMO1, FMO3, GAP43, GDF10, GSC, HOXA5, HSD11B2, HSPA6, HTRA3, ICAM5, ID4, IFI27, IFIT3, INA, KCNMB1, KRT14, KRT17, KRT34, IGFL3, LOC92196, MFAP5, MASP1, MEOX1, MEOX2, MMP1, MX1, MYBPH, MYH3, MYH11, MYL4, IL32, NLGN4X, NPPB, OGN, OSR2, PAX2, PAX9, PENK, PITX2, PRELP, PRG4, PRRX1, RARRES1, RELN, RGMA, SFRP2, SMOC1, SMOC2, SOD3, SYT12, TAC1, TNFSF7, TRH, TSLP, TUBB4, UGT2B7, WISP2, ZD52F10, ZIC1 and ZIC2; the gene expression markers for the cell line B16 are: AKR1C1, BMP4, CLDN11, FST, GDF5, HTRA3, IL1R1, KRT19, KRT34, MFAP5, MGP, MMP1, OSR2, PODN, POSTN, PRG4, PRRX1, RARRES1, S100A4, SOD3, THY1 and ZIC1 and are negative for the markers: ACTC, AGC1, ALDH1A1, AREG, C6, C7, C20orf103, CCDC3, CDH3, CNTNAP2, DKK2, EMID1, FGFR3, FMO3, FOXF1, FOXF2, GABRB1, GDF10, HSD11B2, HSD17B2, HSPA6, ID4, IGF2, INA, LAMC2, IGFL3, LOC92196, MEOX1, MSX1, MYBPH, MYH11, MYL4, NLGN4X, NPAS1, NPPB, OLR1, PAX2, PAX9, PROM1, PTPRN, RASD1, RGS1, SLITRK6, SMOC1, SMOC2, SNAP25, TAC1, RSPO3, TNNT2, TUBB4, ZD52F10 and ZIC2; the cell line C4ELS5.1 is positive for the markers: AKR1C1, C7, CDH6, COL15A1, DIO2, FMO1, FMO3, FOXF2, IGF2, IL1R1, KRT19, LAMC2, TMEM119, PODN, PRRX1, PRRX2, RGMA, SFRP2, TAC1, TFPI2 and RSPO3 and are negative for the markers: ACTC, AGC1, ALDH1A1, ANXA8, APCDD1, AQP1, AREG, ATP8B4, BEX1, CFB, BMP4, C3, C20orf103, CCDC3, CDH3, CLDN11, CNTNAP2, COMP, COP1, CRLF1, CRYAB, CXADR, DKK2, DLK1, EGR2, EMID1, FGFR3, FOXF1, GABRB1, GAP43, GDF10, GJB2, HOXA5, HSD17B2, HSPA6, HSPB3, ICAM5, ID4, IF127, KRT14, KRT17, KRT34, IGFL3, LOC92196, MFAP5, MEOX1, MEOX2, MGP, MMP1, MSX1, MSX2, MX1, MYBPH, MYH3, MYH11, MYL4, IL32, NLGN4X, TAGLN3, NPAS1, NPPB, OLR1, PAX2, PAX9, PENK, PITX2, POSTN, PRELP, PROM1, PTPRN, RARRES1, RELN, RGS1, RPS4Y2, SMOC1, SMOC2, STMN2, THY1, TNFSF7, TNNT2, TRH, TUBB4, UGT2B7, ZD52F10, ZIC1 and ZIC2; for the cell line CM02 they are: AQP1, CD24, CDH6, HTRA3, KRT19, KRT34, TAGLN3, RELN, S100A4, SFRP2, SRCRB4D and UGT2B7 and are negative for the markers: AGC1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GAP43, GSC, HOXA5, HSD11B2, HSPA6, HSPB3, IF127, IFIT3, IGF2, KRT14, MFAP5, MASP1, MEOX2, MYH3, NPAS1, OGN, OLR1, OSR2, PAX9, PDE1A, PENK, PRG4, PROM1, PTPRN, RARRES1, RASD1, RGS1, SERPINA3, SLITRK6, SMOC1, SMOC2, SNAP25, SOD3, STMN2, TAC1, TRH, TSLP, TUBB4 and WISP2; for the cell line E33 they are: AQP1, PRSS35, CD24, CDH6, CLDN11, CRIP1, CRYAB, DKK2, HTRA3, KRT17, KRT19, KRT34, LOC92196, MFAP5, MGP, MYH11, TAGLN3, POSTN, S100A4, SRCRB4D, UGT2B7, ZIC1 and ZIC2 and are negative for the markers: AGC1, AKR1C1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GDF5, GJB2, GSC, HOXA5, HSD11B2, HSPA6, HSPB3, IF127, IFIT3, IGF2, TMEM119, IGFL3, MASP1, MX1, MYBPH, NPAS1, NPPB, OGN, OLR1, OSR2, PAX9, PDE1A, PENK, PITX2, PRG4, PROM1, PTPRN, RARRES1, RASD1, RGMA, RGS1, SERPINA3, SFRP2, SLITRK6, SMOC1, SMOC2, SNAP25, STMN2, TAC1, RSPO3, TRH, TSLP, TUBB4, WISP2 and ZD52F10; for the cell line E68 they are: CD24, CRIP1, CRYAB, HTRA3, KRT17, KRT19, TAGLN3, UGT2B7, ZIC1 and ZIC2 and are negative for the markers: AGC1, AREG, ATP8B4, C6, C7, CDH3, COP1, CRLF1, DLK1, DPT, TMEM100, FMO1, FMO3, FOXF1, FOXF2, GSC, HOXA5, HSD11B2, HSPA6, HSPB3, IGF2, LAMC2, IGFL3, MEOX1, MEOX2, MMP1, MYBPH, MYH3, NPAS1, OGN, PAX9, PITX2, PRG4, PROM1, RARRES1, RGS1, SMOC2, TAC1, RSPO3, TRH, TSLP and WISP2; for the cell line EN13 they are: CDH6, DLK1, FOXF1, FST, HTRA3, IGF2, IL1R1, MSX1, POSTN, SOD3, ZIC1 and ZIC2 and are negative for the markers: ACTC, ALDH1A1, ANXA8, ATP8B4, BMP4, C3, C20orf103, CCDC3, CD24, CDH3, CLDN11, CNTNAP2, COMP, CRYAB, DIO2, DKK2, GSC, HOXA5, HSD11B2, HSD17B2, HSPA6, HSPB3, IF127, INA, KRT14, KRT17, KRT34, IGFL3, LOC92196, MFAP5, MEOX1, MEOX2, MGP, MMP1, MX1, MYH3, MYH11, MYL4, IL32, NPAS1, NPPB, OLR1, PAX2, PAX9, PDE1A, PENK, PITX2, PROM1, RELN, SFRP2, SMOC2, STMN2, TAC1, RSPO3, THY1, TNFSF7, TNNT2, TRH, TUBB4 and ZD52F10; for the cell line SM22 they are: CDH6, CRLF1, DLK1, FOXF1, FST, GDF5, HTRA3, IGFBP5, IL1R1, MGP, MMP1, MSX1, MSX2, OGN, POSTN, PRRX2, PTN, RGMA, SOD3, SRCRB4D, STMN2, TSLP, ZD52F10 and ZIC1 and is negative for the markers: AGC1, ALDH1A1, ANXA8, APCDD1, AQP1, AREG, BMP4, C3, C6, C7, C20orf103, CCDC3, CDH3, CLDN11, CNTNAP2, COL15A1, CRIP1, CXADR, DIO2, DKK2, DPT, TMEM100, FMO1, FOXF2, GDF10, GJB2, GSC, HOXA5, HSD11B2, HSD17B2, HSPA6, HSPB3, ICAM5, IF127, INA, KRT14, KRT17, KRT34, LAMC2, TMEM119, IGFL3, LOC92196, MFAP5, MASP1, MEOX1, MEOX2, MX1, MYBPH, MYH3, MYH11, MYL4, IL32, NLGN4X, NPAS1, NPPB, OLR1, OSR2, PAX2, PAX9, PENK, PITX2, PRG4, PROM1, PTPRN, RARRES1, RASD1, RELN, RGS1, SFRP2, SMOC1, SMOC2, SNAP25, TAC1, RSPO3, TNFSF7, TNNT2, TRH, TUBB4, UGT2B7 and ZIC2; the markers for the cell line T36 are positive for the markers: BEX1, CCDC3, CDH6, CRIP1, FST, HTRA3, KRT17, PTN, S100A4, SRCRB4D, THY1 and ZIC2 and are negative for the markers: AGC1, ALDH1A1, APCDD1, AREG, ATP8B4, C3, C6, C7, PRSS35, C20orf103, CDH3, CLDN11, CNTNAP2, CRLF1, METTL7A, DLK1, DPT, EMID1, FMO1, FMO3, FOXF2, GJB2, GSC, HOXA5, HSD11B2, HSD17B2, HSPA6, HSPB3, IF127, KRT14, IGFL3, LOC92196, MFAP5, MASP1, MEOX1, MEOX2, MGP, MMP1, MYBPH, MYH3, NLGN4X, TAGLN3, NPAS1, NPPB, OGN, OLR1, PAX9, PDE1A, PENK, PRG4, PROM1, PTPRN, RARRES1, RASD1, RELN, RGS1, SLITRK6, SMOC2, SNAP25, STMN2, TAC1, RSPO3, TRH, TUBB4 and WISP2; the cell line W10 is positive for the markers: DLK1, FOXF1, FST, GABRB1, GDF5, HTRA3, IGF2, IGFBP5, IL1R1, POSTN, PTN, SOX11, SRCRB4D and TFPI2 and are negative for the markers: ACTC, AGC1, ALDH1A1, ANXA8, APCDD1, AQP1, AREG, CFB, BMP4, C3, C6, C7, CCDC3, CD24, CDH6, CLDN11, CNTNAP2, COL15A1, COMP, COP1, CRYAB, DKK2, DPT, EGR2, EMID1, FGFR3, FMO1, FMO3, FOXF2, GAP43, GDF10, GSC, HSD11B2, HSD17B2, HSPA6, HSPB3, ID4, IF127, INA, KCNMB1, KRT14, KRT17, KRT34, IGFL3, LOC92196, MEOX1, MEOX2, MX1, MYBPH, MYH3, MYH11, MYL4, IL32, NLGN4X, NPAS1, NPPB, OLR1, PAX2, PAX9, PENK, PITX2, PRELP, PROM1, RARRES1, RASD1, RELN, RGS1, SMOC1, SMOC2, STMN2, SYT12, TAC1, THY1, TNFSF7, TNNT2, TRH, TUBB4, UGT2B7, WISP2, ZIC1 and ZIC2.

The foregoing methods are illustrative and not limiting. Using the teachings provided herein cells and/or cell lines expressing any of the brain growth factors described herein are readily available to one of skill in the art.

Methods and Administration.

In various embodiments, methods of improving recovery of a mammal after cerebral ischemia are provided where the methods involve administering a therapeutically effective amount of a brain growth factor to the infarct cavity in the brain of mammal. In certain embodiments, the administering comprises depositing a depot delivery system into the infarct cavity where the depot delivery system comprises/contains the growth factor(s) and provides sustained release of the growth factor(s), and/or the depot delivery system comprises cells that provide a sustained release of the brain growth factor. In various embodiments the depot delivery system comprises a hydrogel.

Methods of delivering a depot delivery system (e.g., depot formulation or device) into a region of the brain (e.g., an infarct cavity) are known to those of skill in the art. In certain embodiments the depot formulation or device are surgically implanted into the desired site. In other embodiments, particular with respect to depot formulations, the formulation can be delivered into the desired cite by direct injection or through an implanted cannula.

With respect to hydrogel formulations comprising cells as described herein, it was a surprising discovery that the certain hydrogel formulations contemplated herein (e.g. thiolated hyaluronan/thiolated gelatin hydrogels optionally containing heparin) can be readily injected using a fine needle while preserving a high degree of cell viability.

In various embodiments the methods described herein would be practiced as stroke recovery therapy in humans or non-human mammals. In certain embodiments the hydrogel/growth factor (e.g., BDNF) formulation would be given to stroke patients once they are clinically stable from their stroke, and the stroke damage has stopped progressing. This period begins at about day 5 based on clinical studies and animal models of stroke. The stroke cavity would be identified by brain MRI, and used for stereotaxic neurosurgical delivery. The hydrogel/growth factor and/or hydrogel/cell formulation would be directly injected into the stroke cavity in the operating room. In typical embodiments, the window for hydrogel/BDNF therapy after stroke is from 5 days after stroke to one year after stroke. This window is established by the normal recovery period for human stroke. However, in certain circumstances earlier administration/delivery may be merited.

In certain embodiments the depot devices and/or depot formulations described herein are designed to provide a sustained delivery of a therapeutically effective dose of one or more the growth factors (e.g., BDNF, HBEGF, VEGF, IGF-1, bFGF, and the like).

The concentration of growth factor (s) can vary widely, and will typically be selected primarily based on activity of the active ingredient(s), body weight and the like in accordance with the particular mode of administration and/or formulation selected and the subject's needs (see, e.g., Remington's Pharmaceutical Science, 15th ed., Mack Publishing Company, Easton, Pa. (1980), Remington: The Science and Practice of Pharmacy, 21st Ed. 2005, Lippincott Williams & Wilkins, and the like). In certain embodiments amounts, however, will typically be selected to provide dosages ranging from about 0.001, 0.01, 0.11, or 10 mg/kg/day to about 50 mg/kg/day and sometimes higher. In certain embodiments typical dosages range from about 1 mg/kg/day to about 3 mg/kg/day, preferably from about 3 mg/kg/day to about 10 mg/kg/day, more preferably from about 10 mg/kg/day to about 20.0 mg/kg/day, and most preferably from about 20 mg/kg/day to about 50 mg/kg/day. In certain preferred embodiments, dosages range from about 10 mg/kg/day to about 50 mg/kg/day.

In certain embodiments the dosage of cells useful in the delivery of the secreted factors (e.g., BDNF, IGF1, VEGF, HBEGF, bFGF, and the like) or combinations of said factors will depend upon the size and location that would be determined at the time of treatment by a person skilled in the art. From large clinical studies the mean stroke size in humans is 42 mL with a standard deviation of +/−48 mL and median 21 mL at acute time points (24 hours or less). These volumes are mean 83 mL with a standard deviation of +/−75 mL and median 60 mL at 3 months (MR Stroke Collaborative Group (2006) Stroke, 37: 2521-2525). From another study 35.22% of patients have a lesion size of 5-50 mL (at 90 d); 40.87% have a lesion size from 5-75 cc (Whitehead et al. (2009), 40: 1347-1352). While not wishing to provide a limiting description, a typical formulation may provide a HYSTEM®-C volume of one-half the lesion cavity, this means that typical clinically relevant volumes would typically range from about 2.5 mL to about 40 mL. Mixed with the hydrogel prior to cross linking would be 10 million to 1.0 billion cells per mL. While not wishing to provide a limitation, a typical dosage is about 100 million cells/mL with an injected volume determined by the size of the injury."

The foregoing formulations and administration methods are intended to be illustrative and not limiting. It will be appreciated that, using the teaching provided herein, other suitable formulations and modes of administration can be readily devised.

In another embodiment, methods are provided based on the discovery of the role of AMPAR signaling in stroke recovery. The role of AMPAR signaling in stroke recovery was tested using pharmacological gain- and loss-of-function studies. The results indicate that a delayed enhancement in AMPA signaling promotes behavioral recovery after stroke, whereas blocking AMPAR signaling during the same period retards recovery. This recovery effect is mediated via induced BDNF activity within the periinfarct cortex. In contrast to this delayed recovery effect, early enhancement of AMPA signaling increases infarct size. It is believed these findings constitute the first evidence that an inflection point from harm to benefit exists within the first week after stroke for AMPAR function, localizes the effect of AMPAR signaling in functional recovery to the periinfarct tissue that surrounds the stroke, and suggests that pharmacological treatments that enhance AMPAR signaling during the period of recovery after stroke may provide a neural repair therapy.

Accordingly, in certain embodiments, methods of improving recovery of a mammal after an ischemic event (cerebral ischemia) are provided. In various embodiments the methods involve administering an agent to the mammal that enhances AMPA signaling, wherein said agent is administered after a delay period from the onset of the ischemic event; and wherein the agent directly or indirectly induces BDNF expression and/or activity. In various embodiments the agent is not administered until AMPAR signaling switches from promoting cell death to promoting behavioral recovery.

A wide variety of AMPA receptor potentiators are useful in methods described herein, including ampakines (see, e.g., PCT Publication No: WO 94/02475 (PCT/US93/06916), WO98/12185, U.S. Pat. Nos. 5,773,434, 6,030,968, 6,274, 600, 6,166,008, and U.S. Patent Pub. 2005/0228019 A1 all of which are incorporated herein by reference in their entirety for all purposes); LY404187, LY 392098, LY503430, and derivatives thereof (produced by Eli Lilly, Inc.); CX546 and derivatives thereof; CX614 and derivatives thereof; S18986-1 and derivatives thereof; benzoxazine AMPA receptor potentiators and derivatives thereof (see, e.g., U.S. Pat. Nos. 5,736,543, 5,962,447, 5,773,434 and 5,985,871 which are incorporated herein by reference in their entirety for all purposes); heteroatom substituted benzoyl AMPA receptor potentiators and derivatives thereof (see, e.g., U.S. Pat. Nos. 5,891,876, 5,747,492, and 5,852, 008, which are herein incorporated by reference in their entirety for all purposes); benzoyl piperidines/pyrrolidines AMPA receptor potentiators and derivatives thereof as (see, e.g., U.S. Pat. No. 5,650,409, which is incorporated herein by reference in its entirety for all purposes); benzofurazan carboxamide AMPA receptor potentiators and derivatives thereof (see, e.g., U.S. Pat. Nos. 6,110,935, 6,313,1315 and 6,730,677, which are incorporated herein by reference for all purposes); 7-chloro-3-methyl-3-4-dihydro-2H-1,2,4 benzo-thiadiazine S,S, dioxide and derivatives thereof (see, e.g., Zivkovic et al. (1995), *J. Pharmacol. Exp. Therap.*, 272: 300-309; Thompson et al. (1995) *Proc. Natl. Acad. Sci., USA*, 92: 7667-7671).

Illustrative ampakines include, but are not limited to CX546 (1-(1,4-benzodioxan-6-yl carbonyl) piperidine), CX516 (1-quinoxalan-6yl-carbonyl) piperidine), CX614 (2H, 3H, 6aH pyrrolidino[2",1"-3',2']1,3-oxazino[6',5'-5,4] benzo[e]1,4-dioxan-10-one), and CX929.

In certain embodiments particular compounds of interest include, but are not limited to: aniracetam, 7-chloro-3-methyl-3-4-dihydro-2H-1,2,4 benzothiadiazine S,S, dioxide, (see, e.g., Zivkovic et al. (1995) *J. Pharmacol. Exp. Therap.*, 272: 300-309; Thompson et al. (1995) *Proc. Natl. Acad. Sci., USA*, 92:7667-7671), which is incorporated herein by reference for the compounds listed therein.

In various embodiments the ampakine(s) include one or more high-impact ampakines.

In certain embodiments the methods described herein utilize ampakines as described, for example, in U.S. Pat. No. 6,166,008. Such ampakines include, compounds according to formula I of U.S. Pat. No. 6,166,008:

In certain embodiments the methods utilizing ampakines expressly exclude subjects diagnosed as having and/or under treatment for one or more conditions selected from the group consisting of Alzheimer's disease (AD), attention deficit hyperactivity disorder (ADHD), Parkinson's disease, a sleep disorder, depression, fragile X disorder, mental retardation, and an opiate-induced or other respiratory depression.

EXAMPLES

The following examples are offered to illustrate, but not to limit the claimed invention.

Example 1

AMPA Receptor-Induced Local Brain-Derived Neurotrophic Factor Signaling Mediates Motor Recovery after Stroke Stroke is the leading cause of adult disability. Recovery after stroke shares similar molecular and cellular properties with learning and memory. A main component of learning-induced plasticity involves signaling through AMPA receptors (AMPARs). We systematically tested the role of AMPAR function in motor recovery in a mouse model of focal stroke. AMPAR function controls functional recovery beginning 5 d after the stroke. Positive allosteric modulators of AMPARs enhance recovery of limb control when administered after a delay from the stroke. Conversely, AMPAR antagonists impair motor recovery. The contributions of AMPARs to recovery are mediated by release of brain-derived neurotrophic factor (BDNF) in periinfarct cortex, as blocking local BDNF function in periinfarct cortex blocks AMPAR-mediated recovery and prevents the normal pattern of motor recovery. In contrast to a delayed AMPAR role in motor recovery, early administration of AMPAR agonists after stroke increases stroke damage. These findings indicate that the role of glutamate signaling through the AMPAR changes over time in stroke: early potentiation of AMPAR signaling worsens stroke damage, whereas later potentiation of the same signaling system improves functional recovery.

Materials and Methods

Photothrombosis

Focal stroke was induced by photothrombosis in adult male C57BL/6 mice weighing 20-25 g as previously described (Clarkson et al. (2010) Nature 468: 305-309).

In Vivo Drug Dosing

CX1837 (0.33 and 1 mg/kg) and CX1739 (3 and 30 mg/kg) were dissolved in 30% hydroxypropyl_β-cyclodextran (HPCD) (made 1:1 in 0.9% saline and distilled $H_2O$) and administered intraperitoneally twice daily starting 5 d after stroke for a period of 6 weeks. The AMPAR antagonist CFM2 (50 µM/kg) (De Sarro et al. (1999) Eur. J. Pharmacol., 368: 149-159) was administered intraperitoneally twice daily for 6 weeks.

A hyaluronan/heparin sulfate proteoglycan biopolymer hydrogel (Extracel-HP, a.k.a., HYSTEM®-HP; BioTime,) was used to locally deliver TrkB-Fc (5 µg/ml) and human IgG-Fc (antibody and vehicle control) to the periinfarct cortex (Li et al. (2010) Nat. Neurosci. 13: 1496-1504). This hydrogel was chosen because it is composed of naturally occurring brain extracellular matrix constituents; remains liquid for a period after mixing so that it can be injected into the brain through a small, minimally invasive needle; and will gel within the stroke cavity, conforming to the boundaries of this cavity. We have shown that this hydrogel releases small and large proteins for up to 4 weeks from the infarct cavity after stroke. Five days after stroke, 10 µl of Extracel-HP (HYSTEM®-HP), impregnated with TrkB-Fc (5 µg/ml) or human IgG-Fc (vehicle), was injected directly into the stroke infarct cavity using a 30 gauge needle attached to a Hamilton syringe. Extracel-HP was prepared according to the manufacturer's instructions. The antibody or antibody conjugate was added to Heprasil (component 1 of hydrogel), followed by addition of Extracel (component 2 of hydrogel) in a 4:1 ratio. Extracel-HP impregnated with antibody was injected immediately after preparation into the stroke cavity at stereotaxic coordinates 0 mm anteroposterior (AP), 1.5 mm mediolateral (ML), and 0.75 mm dorsoventral (DV). In vitro studies indicate that, at 37° C. in an aqueous environment, the liquid constituents form a gel within 20 min. The TrkB-Fc-impregnated biopolymer hydrogel was administered alone and in concert with twice daily intraperitoneal administration of CX1837 (1 mg/kg) starting from 5 d after stroke for 6 weeks.

Behavioral Assessment

Animals were tested once on both the grid-walking and cylinder tasks, 1 week before surgery to establish baseline performance levels. For the reaching task, mice were trained for a period of 14 d and subsequently tested on day 15 to establish a baseline reading. For all of the studies, animals were tested on weeks 1, 2, 4, and 6 after stroke at approximately the same time each day at the end of their dark cycle. Behaviors were scored by observers who were blind to the treatment group of the animals in the study as previously described (Clarkson et al. (2010) Nature 468: 305-309).

Grid-Walking and Spontaneous-Forelimb (Cylinder) Task.

Both gridwalking and cylinder tasks were performed as previously described (Id.).

Single-Pellet Skilled-Reaching Task.

For loss-of-function studies assessing CFM2, the single-pellet skilled-reaching task was used (Conner et al. (2005) Neuron 46: 173-179). Before stroke, animals were trained for 3 weeks to successfully reach and retrieve 20 mg sugar pellets (Bio-Serv). A three lane Plexiglas reaching apparatus (30 cm deep, 10 cm wide, and 30 cm high for each lane) was constructed to allow simultaneous recording of three animals. Each lane consists of two 5 mm slots situated against the front-right and front-left walls of the chamber to force the mouse the reach for the pellets using either their right or left forepaws. A 5-mm-thick plastic shelf was mounted 15 mm from the floor at the front of the box.

During the training period, mice were fasted to 90% of their body weight and maintained at this level for the full 3 week training period. Animals were habituated during the first week by placing them into the lanes two times for 7.5 min each time with a 5 min recovery period in their home cage. Sugar pellets were freely available on the lane floor within tongue reach as well as just outside the slot opening. Pellets were gradually removed from the floor until only the pellets just outside of slot remained and the mice were forced to retrieve the pellets. The second 2 weeks consisted of training the mice one time for 15 min to retrieve 15 pellets through the slot. Pellets were gradually moved further away from the slot (~1 cm maximal distance) to force the mice to use their paw and not their tongue.

Reaching Success.

All mice were fasted the night before testing. Pellets were presented one at a time and reaches were recorded with a Canon VIXIA HV30 video recorder. Each animal was presented with a total of 15 pellets during each 15 min test period. If an animal reached through the slot and obtained/grasped a food pellet and brought the pellet back through the slot, the reach was scored as a success. If an animal knocked the pellet away or dropped the pellet after grasping it, the reach was scored as a miss. The performance of each mouse was scored as follows: percentage success=(number of successful retrievals/15)*100.

BDA Injection and Infarct Size

Eight week poststroke animals were injected with the neuroanatomical tracer 10% biotinylated dextran amine (300 nl of BDA; 10,000 MW; Invitrogen). BDA was pressure injected into the forelimb motor cortex (AP, 1.5; ML, 1.75; DV, 0.75) using a picospritzer with pulled glass micropipettes (tip diameter, 15-20_m), using previously described stereotaxic techniques (Carmichael et al. (2001) Neurobiol. Dis., 8: 910-922). Seven days after BDA injection, animals were perfused with 0.1 M PBS followed by 4% paraformaldehyde. The cortex was removed from the subcortical tissue and flattened precisely between two glass slides separated by 2 mm steel washers to ensure equivalent cortical thickness across subjects. Tangential cortical sections (40 µm) were generated using a sliding microtome and stored in cryoprotectant at −20° C. Tangential cortical sections were removed from cryoprotectant and rinsed in 0.1 M KPBS. Sections were processed for cytochrome oxidase histochemistry to visualize the somatosensory body map. BDA was visualized in the same sections using the Standard Vectastain Elite kit (Vector Laboratories) and the chromagen DAB, enhanced with cobalt chloride (Carmichael et al. (2001) Neurobiol. Dis., 8: 910-922; Li et al. (2010) Nat. Neurosci. 13: 1496-1504). Sections were mounted on subbed slides, dehydrated in ascending alcohols, cleared in xylenes, and coverslipped. The distribution of BDA-labeled cell bodies and axons were plotted in tangential sections graphed on scatter plots overlaid on physical maps through the barrel field of the cortex (Id.). For the histological assessment of infarct size, brains were processed 7 d after stroke using cresyl violet as previously described (Ohab et al. (2006) J. Neurosci. 26: 13007-13016; Clarkson et al. (2010) Nature 468: 305-309).

Stereological Quantification of Axonal Sprouting.

The BDA injection volume was measured by calculating the average injection core volume for each treatment group.

The average BDA injection area in each section, determined by outlining the limit of extracellular tracer deposition, was multiplied by the sum of the thickness of the section and then summed for all sections in the series. Anterior/posterior and medial/lateral BDA injection location was analyzed by measuring the distance from the center of the injection site to the rostral edge of the tissue and the midline of the cortex, respectively (Li et al. (2010) *Nat. Neurosci.* 13: 1496-1504). The size and location of each BDA injection did not vary significantly across animals or by treatment condition (see FIG. 9).

Sprouting was quantified by digitally marking each BDA-positive cell in the superficial layers of the cortex (layers 2/3) from each group with a digitizing microscope/computer-controlled motorized stage system (Leica Microsystems; Lud1 Electronic Products) and interfaced camera (MicroFire) with a neuroanatomical analysis program (MicroBright-Field). BDA-positive cells were marked in x/y coordinates relative to the center of the injection site by an observer blind to the treatment conditions. The hardware provides a labeling precision of ±5 μm in mapping the location of all BDA cells within the tangential cortical sections. This process generates an x/y plot of the location of all labeled cells in each brain section. The x/y plots of each brain from each experimental group were registered with respect to the injection site and coregistered with functionally relevant anatomical regions, produced by the staining of the mouse somatosensory body map in cytochrome oxidase, to generate a composite axonal map for each treatment condition (Carmichael et al. (2001) *Neurobiol. Dis.,* 8: 910-922; Li et al. (2010) *Nat. Neurosci.* 13: 1496-1504). Custom software was developed to produce quantitative connectional maps that consist of pixels, with the number of axons in each pixel mapped in register with anatomical brain structures. Polar plots representing these circular data illustrate both location and direction of sprouting. Polygons represent the 70th percentile of the distances of BDA-labeled axons from the injection site in each segment of the graph. Weighted polar vectors represent the median vector multiplied by the median of the normal distribution of the number of points in a given segment of the graph. The normal distribution is the axonal projection pattern that would occur if neurons projected equally and radially from the injection site. These maps were then analyzed for statistically significant differences in connectional profiles between groups.

Statistical Analysis of Axonal Sprouting.

For quantitative connectional maps, two statistical analysis paradigms were used to determine significant differences. First, scatter plots were analyzed using Hotelling's $T^2$ test for spatial correlation. For data with a common covariance matrix, such as the map of BDA-labeled cell bodies in tangential cortical sections, Hotelling's $T^2$ method tests the hypothesis of multivariate mean equality: that the means for the set outcome variable (axonal location for each animal, averaged by experimental condition) are equivalent across groups. The $T^2$ statistic is the analog of Student's two-group t statistic for testing equality of group means for a single outcome variable. Values of p were computed without Gaussian assumptions via a bootstrap method, with 1000 resamplings. Values of p represent the ridge estimate of (log) Hotelling's $T^2$ for the comparison between two groups. A mask with a radius of 500_m was applied around the injection site to account for the uniformity of the injection site itself and immediately adjacent BDA labeling across groups, regardless of sprouting pattern. A second analysis tool tested for significant differences by location within the cortical hemisphere. This approach uses the polar distribution of projection patterns across treatment groups. For each treatment condition, the x/y coordinate of every BDA-positive cell body was converted to an equivalent polar coordinate relative to the injection site as center (Carmichael et al. (2001) *Neurobiol. Dis.,* 8: 910-922; Dancause et al. (2005) *J. Neurosci.* 25: 10167-0179; Ohab et al. (2006) *J. Neurosci.* 26: 13007-13016) (r, θ). The location of each cell body was transferred to common polar space and a mean projection vector was computed for each treatment group. The projection vector was defined by the angle of projection from the injection site (θ) and distance (length of vector, r) from the center of the injection site (forelimb motor cortex).

ELISA and Immunoblotting Analysis

Tissue was collected from around the stroke site from stroke plus vehicle, stroke plus CX1837 (1 mg/kg), and stroke plus CX1739 (3 mg/kg), and control groups 7 d after stroke. Cortical tissue was dissected in a 1 mm radius around the stroke infarct core, including the core itself, and flash frozen on dry ice.

Equal volumes of tissue were homogenized in 100 ml of homogenization buffer [Complete Protease Inhibitor Tablet (Invitrogen), 1 mM phenylmethylsulfonylfluoride, 50 mM Tris-HCl, 5 mM EDTA, 10 mM EGTA, 1% Triton X-100] for ~1 min. Tissue and homogenization buffer were incubated on ice for 30 min, followed by a 5 min spin at 14,000 rpm. The supernatant was collected and total protein concentrations were determined using the DC Protein Assay (Bio-Rad). BDNF was measured using the BDNF ELISA Emax Immunoassay System (Promega) as per the manufacturer's instructions. BDNF levels were determined relative to a standard curve constructed from measures of kit-supplied BDNF protein standards (0-500 pg of BDNF protein) that were assayed simultaneously with the experimental samples. BDNF levels are expressed as picograms of BDNF per 100 μg of sample protein.

For immunoblotting experiments, protein (10 μg) was loaded onto a 12% SDS-polyacrylamide gel, subjected to electrophoresis, and transferred to a pure nitrocellulose membrane (GE Healthcare). The membrane was blocked in 10% nonfat milk and probed with polyclonal antibodies specific for anti-TrkB (1:1000; Santa Cruz Biotechnology) and anti-p-Trk (1:5000; Santa Cruz Biotechnology). The blots were incubated with peroxidase-labeled anti-rabbit IgG (1:2000; Vector Laboratories) and immunoreactive proteins were visualized using enhanced chemiluminescence (GE Healthcare). β-Actin was used as a loading control (1:5000; Abcam). Optical density (OD) was determined using the NIH ImageJ software. Pixel intensities were converted to OD using the calibration curve of the software, and background-subtracted values were expressed as OD/100 g total protein.

In Vivo Electrophysiological Recordings

Male Long-Evans rats (250-350 g) were anesthetized by pentobarbital (60 mg/kg, i.p.) and maintained under anesthesia by pentobarbital infusion (2-4 mg·kg$^{-1}$·h$^{-1}$). Under anesthesia, animals were placed in a stereotaxic frame and small holes were drilled into the skull of the left hemisphere to allow the positioning of a stimulating electrode (−7.8 to −8.1 AP; 4.2 to 4.4 ML) and a recording electrode (−3.0 to −3.3 AP; 1.6 to 2.2 ML). A monopolar stainless-steel stimulating electrode (175 μm, insulated with Formvar) was lowered into the perforant path together with a platinum/iridium recording electrode (75 μm) into the hilus of the dentate gyms of the hippocampus. The current used to elicit an evoked potential was adjusted to produce a response size 50-60% of the maximal spike-free amplitude. Evoked hilar EPSPs were recorded in response to single-pulse stimulation delivered at a frequency of one pulse per 20 s. After 20-30 min of stable baseline recordings, CX1837 or CX1739 in 33% HPCD were injected intraperitoneally and field potentials recorded continuously every 20 s for an additional 80-100 min (see FIG. 4).

Data acquisition and analysis was performed using commercially available software (NAC and NACSHOW). The amplitude, half-width, and area of the EPSPs were measured for each stimulation pulse, and the effects of CX1837 on EPSPs were compared with baseline EPSPs using a two-tailed, two-sample equal-variance Student t test.

Statistical Analysis

All data are expressed as mean±SEM. For behavioral testing, differences between treatment groups were analyzed using two-way ANOVA with repeated-measures and Newman-Keuls' multiple pairwise comparisons for post hoc comparisons. BDA projection profiles between controls and experimental groups were analyzed using Hotelling's t test (Carmichael et al. (2001) *Neurobiol. Dis.*, 8: 910-922; Li et al. (2010) *Nat. Neurosci.* 13: 1496-1504). The level of significance was set at $p<0.05$. Samples sizes for all the experiments were as follows: n=8-10 per group for behavior; n=4 per group for histology, BDA quantification, and immunoblotting; and n=4 per group for in vivo electrophysiology.

Results

Positive Modulators of AMPAR Signaling Improve Motor Recovery after Stroke

Figure 2:
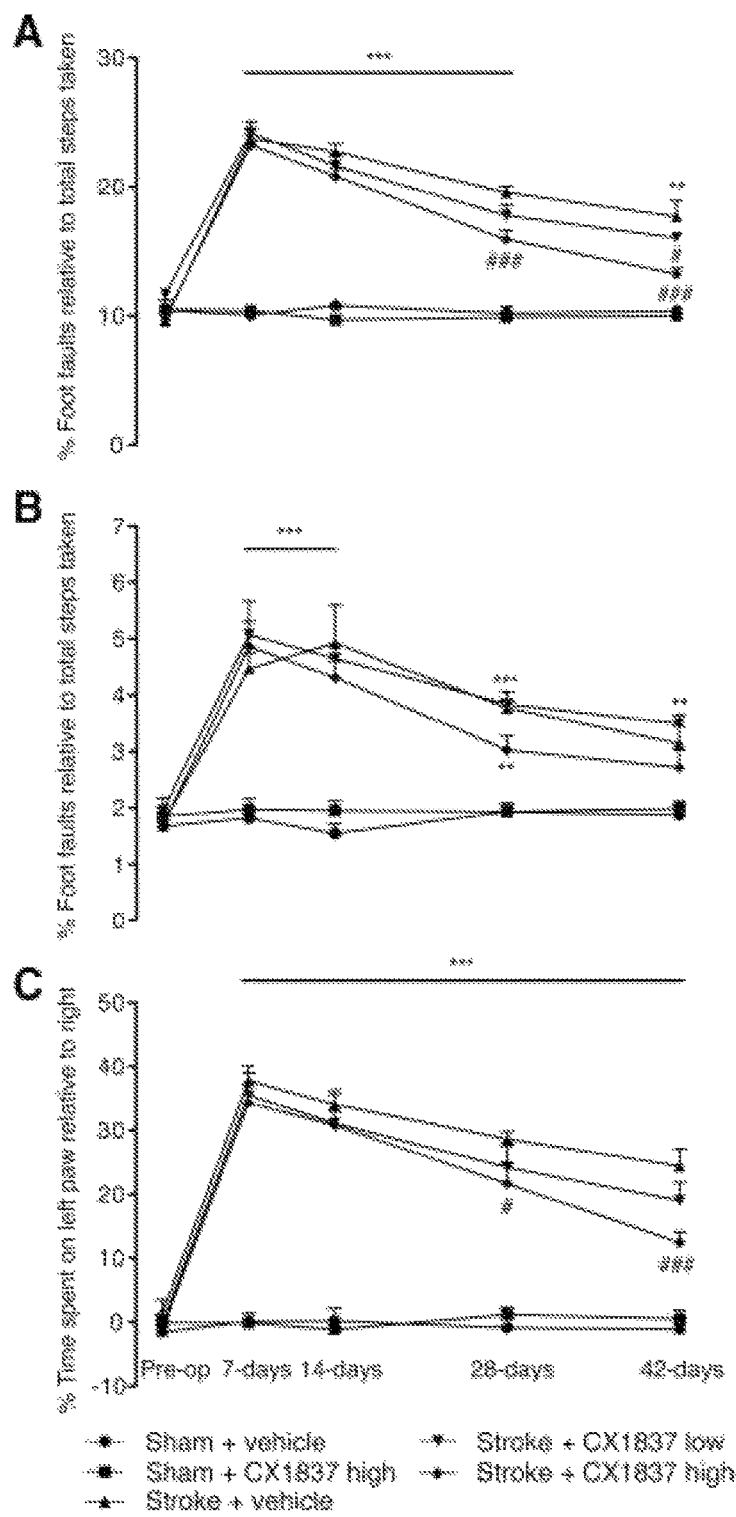
FIG. 2, panels A-C, illustrate behavioral recovery in the presence of the high-impact ampakine, CX1837. Behavioral recovery after stroke was assessed on grid-walking (panels A and B) and cylinder/forelimb asymmetry (panel C) tasks. Analysis of forelimb (panel A) and hindlimb (panel B) footfaults revealed a significant increase in the number of footfaults compared with baseline and time-matched sham-treated controls. Administration of CX1837 (0.33 or 1 mg/kg) resulted in a gradual yet steady dose-dependent decrease in the number of footfaults compared with vehicle (30% HPCD)-treated stroke animals. Assessment of forelimb asymmetry using the cylinder task (panel C) showed that the mice had a greater tendency to spend more time on their left forepaw poststroke as revealed by an increase in the left/right ratio. Treatment with CX1837 resulted in a steady dose-dependent gain of function of the right forelimb. Data are shown as mean±SEM for n=8 per group. $p<0.01$, $*p<0.001$ compared with sham controls; $\#p<0.05$, $\#\#\#p<0.001$ compared with stroke plus vehicle-treated animals.

Mice were given a stroke in forelimb motor cortex and received behavioral testing of forelimb and hindlimb motor function for 6 weeks after stroke. Stroke causes mice to exhibit limb use deficits for at least 6 weeks after the infarct, with mice still exhibiting 55% impairment in forelimb function on the grid walk and 65% on the cylinder task. Mice have an increase in the number of footfaults (both right-forelimb and hindlimb) on a grid walk task, and an increased use of the ipsilateral forelimb to the stroke in spontaneous use on the cylinder task (FIG. 2).

To test the effect of AMPAR signaling in motor recovery after stroke with an in vivo gain-of-function assay, we administered both BDNF-inducing (CX1837) and non-BDNF-inducing (CX1739) ampakines beginning 5 d after stroke, a time in which most cell death is complete (Braun et al. (1996) *Acta. Neuropathol.*, 92:255-263; Lipton (1999) *Physiol. Rev.* 79: 1431-1568; Ohab et al. (2006) *J. Neurosci.* 26: 13007-13016). Both classes of ampakines promote an increase in ionotropic conductance in response to glutamate binding to the AMPAR, whereas only CX1837 promotes an elevation in BDNF levels (Lauterborn et al. (2003) *J. Pharmacol. Exp. Ther.*, 307: 297-305; Lauterborn et al. (2009) *Neuroscience* 159: 283-295; Simmons et al. (2009) *Proc. Natl. Acad. Sci. U.S.A.*, 106: 4906-4911). CX1837 and CX1739 both cross the blood-brain barrier (BBB) when given systemically and activate excitatory signaling (see FIG. 2). CX1837 (0.33 or 1 mg/kg, i.p., bid) promotes a dose dependent gain of function in the impaired forelimb (FIG. 2, panels A, C), from week 4 after stroke onward, with only a mild impairment still evident by week 6 after stroke (FIG. 2, panels A, C). Animals treated with CX1837 also showed a mild gain of function with the right hindlimb (FIG. 2, panel B).

Figure 3:
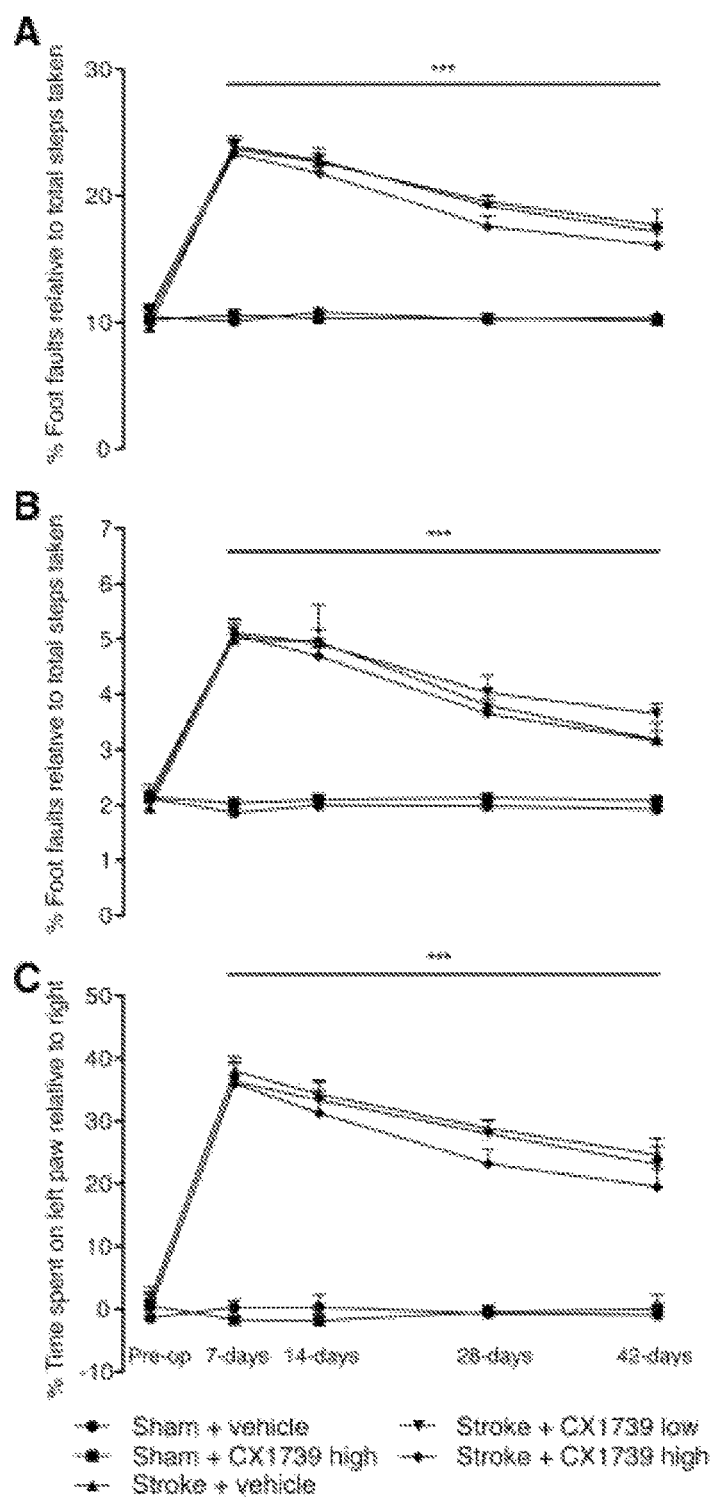
FIG. 3, panels A-C, illustrate behavioral recovery in the presence of the low-impact ampakine, CX1739. Behavioral recovery after stroke was assessed on grid-walking (panels A and B) and cylinder/forelimb asymmetry (panel C) tasks. Analysis of forelimb (panel A) and hindlimb (panel B) footfaults revealed a significant increase in the number of footfaults compared with baseline and time-matched sham-treated controls. Administration of CX1739 (3 or 30 mg/kg) resulted in a small yet non-significant decrease in the number of footfaults compared with vehicle-treated stroke animals. Assessment of forelimb asymmetry using the cylinder task (panel C) revealed that treatment with CX1739 did not result in a decrease in the left/ratio and were similar to stroke plus vehicle-treated controls. Data are shown as mean±SEM for n=8 per group. $***p<0.001$ compared with sham controls.

Treatment with CX1739 for 6 weeks resulted in a small decrease in the number of footfaults on the grid-walking task and a small increase in the use of the right-impaired forelimb on the cylinder task (FIG. 3). However, these changes after CX1739 treatment were not significantly (p=0.054) different from stroke plus vehicle-treated controls at either low or high doses (3 or 30 mg/kg, i.p., bid).

CX1837 and CX1739 Freely Cross the BBB to have a Synaptic Effect

Figure 4:
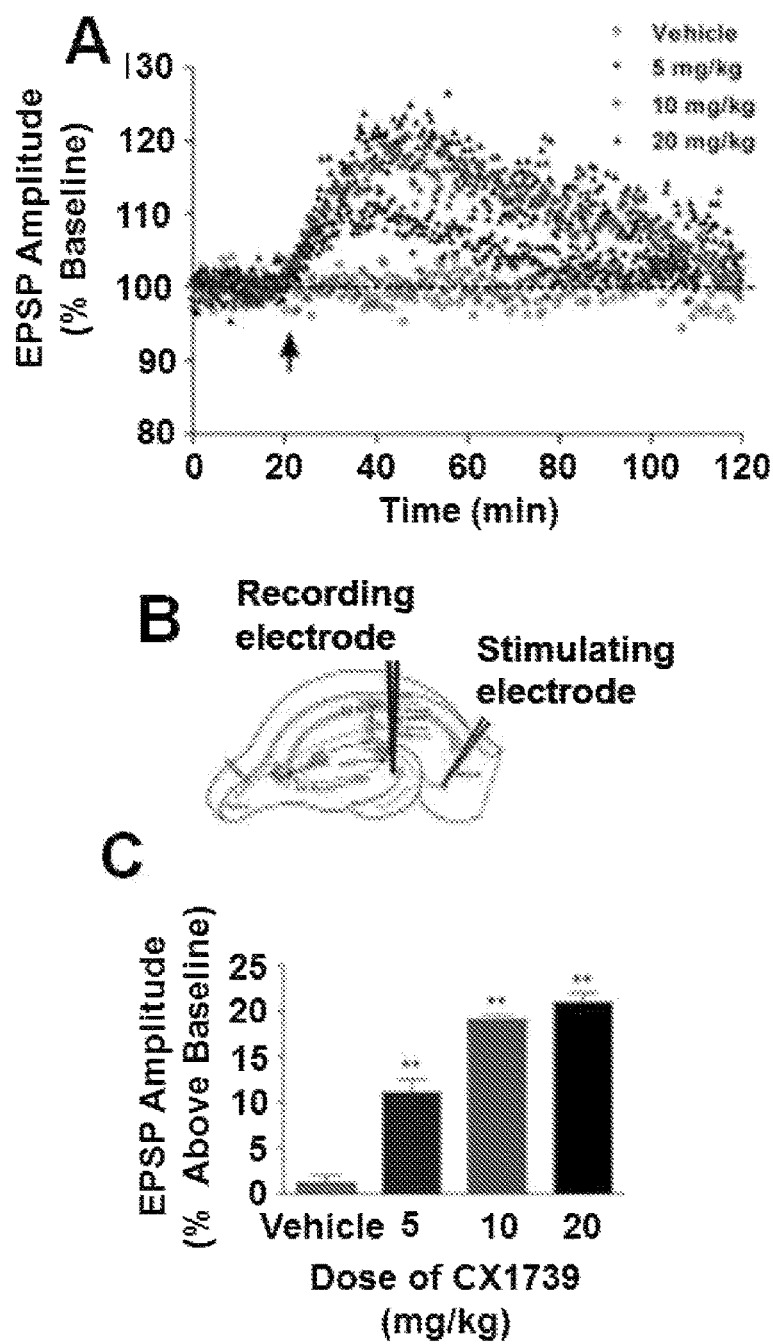
FIG. 4, panels A-E, show the effects of CX1837 and CX1739 on EPSPs. To assess whether CX1837 and CX1739 crossed the BBB and were having an effect synaptically, EPSPs measures were recorded from anesthetized animals in vivo, with the positioning of the electrode shown in panel B. Administration of CX1739 (5-20 mg/kg, i.p.) resulted in an immediate increase in EPSP amplitude (panel A) that was dose dependent (panel B). CX1837 (0.2-10 mg/kg, i.p.) also resulted in an immediate and dose-dependent increase in EPSP amplitude (panel D) that is larger in effect than CX1739. The effect of CX1837 is also dose dependent (panel E). Data points that are shown represent the mean±SEM. N=4 per group. **$p<0.01$ compared with controls, after analysis using a one-way ANOVA and Dunnett's multiple-comparison test.

To assess whether these compounds crossed the BBB and were having an effect synaptically, EPSPs were recorded from anesthetized animals in vivo. CX1837 (0.2-10 mg/kg, i.p.) resulted in an immediate and dose-dependent increase in EPSP amplitude (FIG. 4). Administration of CX1739 (5-20 mg/kg, i.p.) resulted in a similar immediate increase in EPSP amplitude. However, unlike CX1837, the effect was much less, with an excitability ceiling seen after 10 mg/kg (FIG. 4).

AMPA Gain of Function is Attenuated in the Presence of BDNF Blockade

A BDNF-inducing ampakine such as CX1837 may promote motor recovery after stroke because of potentiation of inward cation influx and excitatory signaling after stroke, or via the enhancement of BDNF expression. Furthermore, as CX1837 is administered systemically and freely penetrates the BBB (FIG. 4), the locus within the brain responsible for the regulation of motor recovery after stroke remains unknown. To help delineate a BNDF effect versus an activity-dependent AMPAR-mediated effect, we first measured the induction of BDNF and activation of its tyrosine kinase receptor, TrkB, in stroke alone and after CX1837 treatment. To further isolate the locus of BDNF signaling, local periinfarct BDNF blockade was performed in stroke and in the CX1837 treatment groups.

Figure 5:
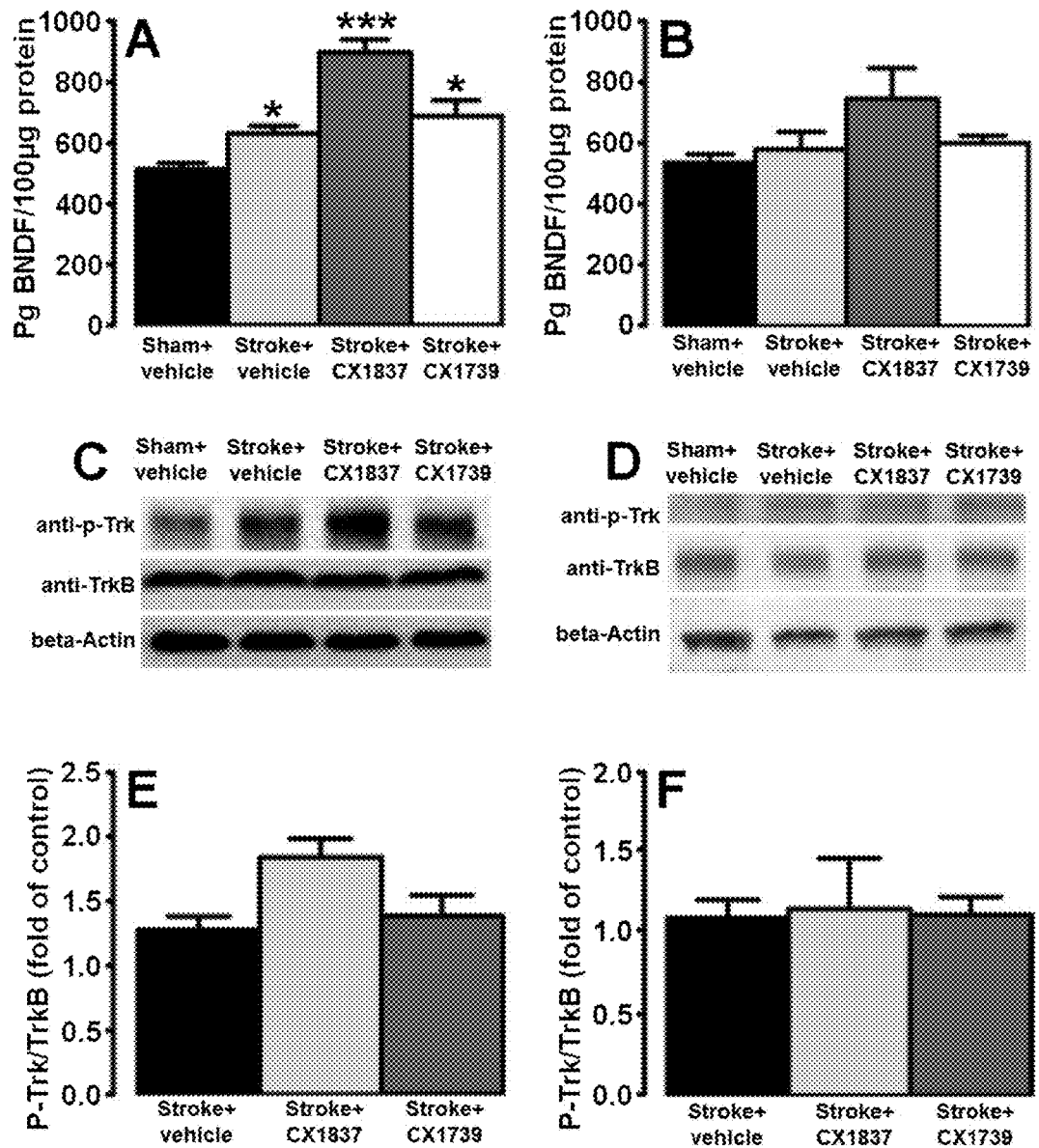
FIG. 5, panels A-F, show ampakine-mediated alterations in BDNF expression. CX1837 mediates BDNF release within the periinfarct cortex poststroke. BDNF expression levels (panel A) were elevated 7 d after stroke. Treatment with CX1837 from day 5 after stroke resulted in a significant increase in BDNF levels, whereas CX1739 did not alter the level of BDNF expression compared with stroke control. No significant changes in BDNF levels were observed on the contralateral hemisphere (panel B). Assessment of BDNF receptor activation TrkB/p-Trk showed a significant increase in activation after CX1837 treatment within the periinfarct cortex poststroke (panels C and E). Assessment of TrkB/p-Trk in the contralateral hemisphere showed no changes between treatment groups (panel s D and F). Data are shown as mean±SEM for n=4 per group. *$p<0.05$, $p<0.01$, *$p<0.001$ compared with sham controls.

BDNF signals via activation and phosphorylation of its TrkB receptor. Studies have previously reported a positive correlation between ampakine-mediated BDNF expression and phosphorylation of TrkB (Jourdi et al. (2009) *J. Neurosci.*, 29: 8688-8697; Lauterborn et al. (2009) *Neuroscience* 159: 283-295). Stroke and CX1837 significantly induce BDNF and BDNF signaling. Stroke induced BDNF in periinfarct cortex compared with control cortex at 7 d after stroke (p<0.05) (FIG. 5, panel A). Treatment with CX1837 resulted in an additional increase in BDNF levels compared with stroke plus vehicle-treated controls (p<0.001). However, treatment with CX1739 did not change the level of BDNF expression compared with stroke plus vehicle-treated animals. There were no significant differences in BDNF levels in the contralateral hemisphere in any stroke or treatment groups (FIG. 5, panel B). In periinfarct cortex, there is a small increase in TrkB phosphorylation in stroke alone compared with control samples. Stroke plus CX1837, however, resulted in a marked increase in TrkB phosphorylation (p<0.01). CX1739 did not change the level of TrkB phosphorylation compared with stroke plus vehicle-treated animals (FIG. 5, panels C, E). No differences in TrkB phosphorylation were observed on the contralateral hemisphere (FIG. 5, panels D, F). These data indicate that BDNF activity and an AMPAR stimulating effect is present only in periinfarct cortex during recovery. Stroke induces an increase in BDNF only in periinfarct cortex. CX1837 enhances this periinfarct BDNF induction and produces a significant activation of its receptor.

Figure 6:
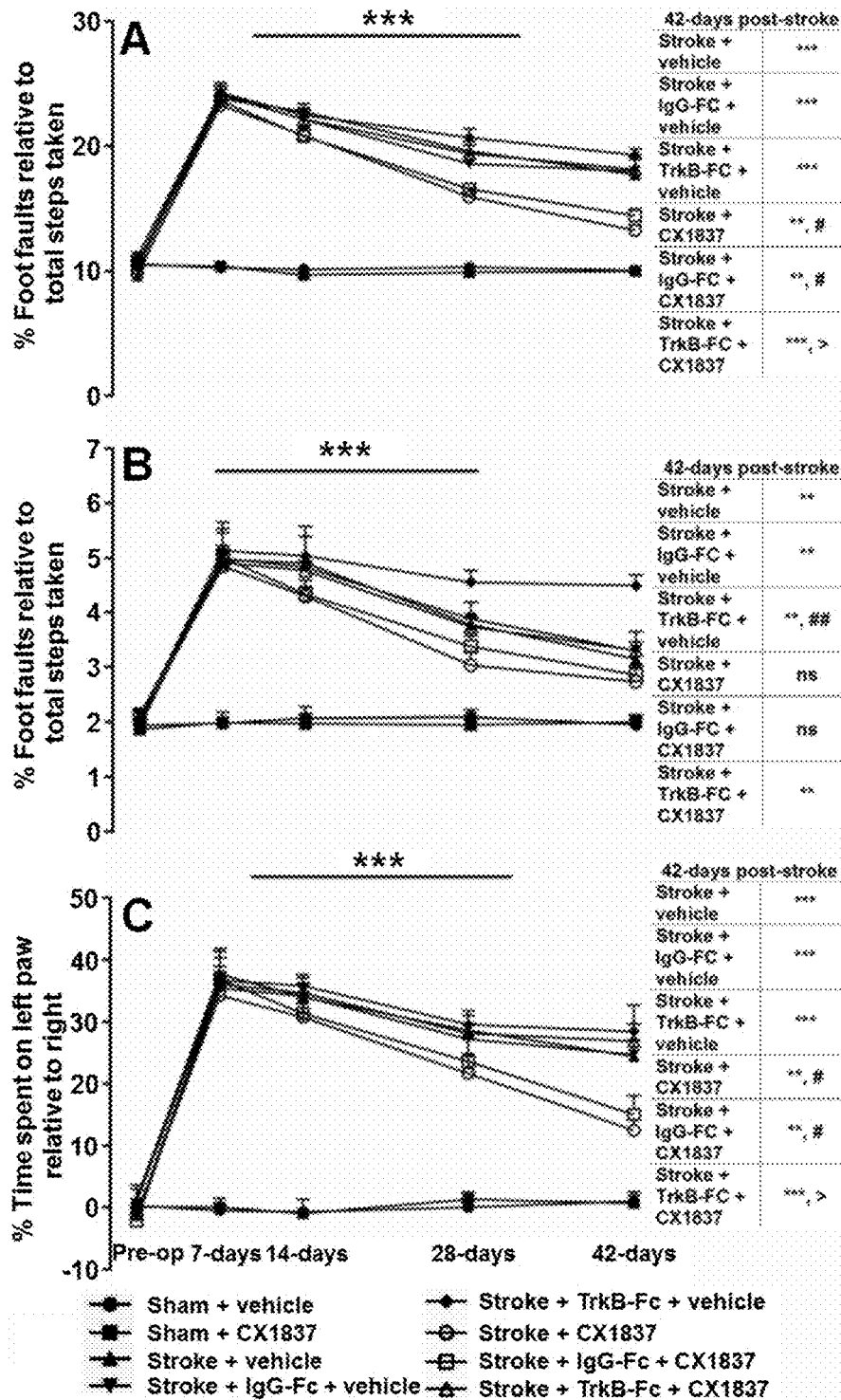
FIG. 6, panels A-C, show the BDNF ligand decoy, TrkB-Fc, negates the CX1837-mediated gain of behavioral function. BDNF blockade within the periinfarct cortex was achieved by infusing TrkB-Fc-impregnated hydrogel into the stroke cavity. Behavioral recovery was assessed after CX1837 treatment in the presence and absence of TrkB-Fc on grid-walking (panels A and B) and cylinder/forelimb asymmetry (panel C) tasks. Implantation of the TrkB-Fc-impregnated hydrogel on day 5 after stroke resulted in a complete blockade of the CX1837-mediated gain of behavioral function on both the grid-walking and cylinder task. Furthermore, vehicle-treated stroke animals that received the TrkB-Fc hydrogel showed impairment in the normal gain of behavioral recovery for hindlimb footfaults (panel B). These results show a requirement for local periinfarct BDNF levels in facilitating functional recovery. The tables next to panels A-C show the statistical comparisons between treatment groups at 42 d after stroke. Data are shown as mean±SEM for n+8 per group. ns, No significance. $p<0.01$, *$p<0.001$ compared with sham controls; ##$p<0.01$, #$p<0.001$ compared with stroke plus vehicle-treated animals; >$p<0.001$ compared with stroke plus CX1837-treated animals.

To determine a behavioral role for normal and CX1837-induced BDNF after stroke, the BDNF receptor decoy, TrkBFc, was locally delivered into periinfarct cortex in the presence and absence of systemically administered CX1837 (1 mg/kg, i.p., bid) beginning 5 d after stroke. Local periinfarct treatment with the TrkB-Fc receptor decoy completely blocked the CX1837-mediated behavioral gain of function (FIG. 6). However, the functional recovery in stroke animals treated with CX1837 (1 mg/kg) in the presence of IgG-Fc control was not blocked. Stroke animals treated with TrkB-Fc alone showed a small decrease in the rate of normal stroke-induced recovery. These findings indicate that the CX1837 induction of BDNF signaling within the periinfarct cortex mediates motor recovery after stroke.

Blockade of AMPA Signaling Impairs Motor Recovery after Stroke

Figure 7:
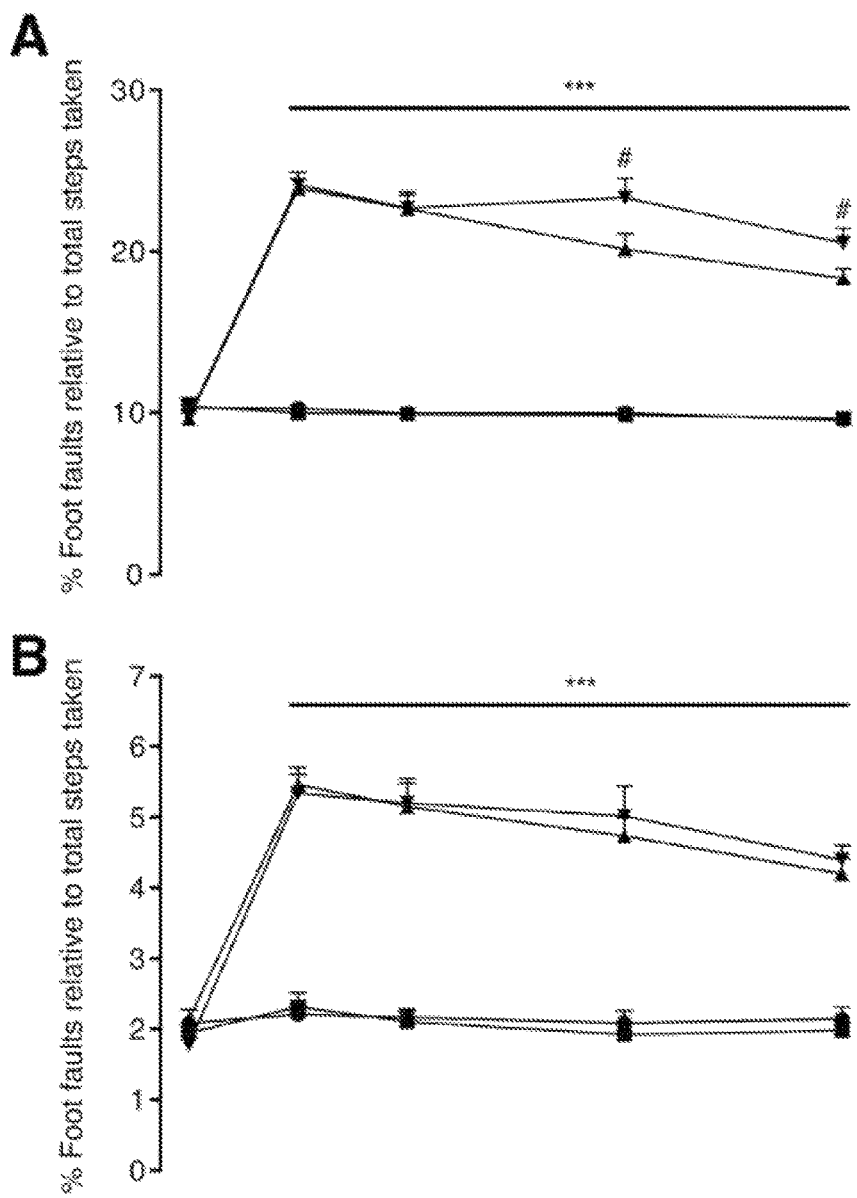
FIG. 7, panels A-D, show that AMPAR antagonism impairs behavioral recovery. Loss of behavioral recovery was assessed after administration of an AMPA receptor selective agonist, CFM2 (50_mol/kg), on grid-walking (panels A and B), cylinder/forelimb asymmetry (panel C), and reaching (panel D) tasks. Treatment with CFM2 resulted in a significant increase in the number of footfaults on the grid-walking task (panel A) and a decrease in the number of pellets successfully retrieved on the reaching task (panel D). Data are shown as mean±SEM for n=10 per group. *$p<0.05$, $p<0.01$, *$p<0.001$ compared with sham controls; #$p<0.05$ compared with stroke plus vehicle-treated animals.

Boosting AMPAR-mediated BDNF signaling in periinfarct cortex promotes motor recovery after stroke in this mouse model. If AMPAR signaling is indeed necessary for motor recovery after stroke, then blocking AMPAR signaling starting 5 d after stroke should impair motor recovery. CFM2, a blood-brain barrier permeable AMPAR antagonist (De Sarro et al. (1999) *Eur. J. Pharmacol.,* 368: 149-159), was administered (50 µmol/kg, i.p., bid) for 6 weeks starting 5 d after stroke. Treatment of CFM2 did not produce general behavioral side effects, such as reduced motor activity, impaired grooming, or weight loss (De Sarro et al., 1999). CFM2 administration results in a significant impairment in the normal gain of motor function after stroke as assessed by normal forelimb movement (FIG. 7, panels A, C). To further test the behavioral effects of AMPAR signaling, we tested AMPAR blockade on a task that normally recovers after stroke, a skilled-reaching behavior. The ability to retrieve food pellets successfully through a small opening using the impaired right forelimb was significantly decreased only at the 1 week time point in normal stroke (FIG. 7, panel D). Treatment with CFM2 impaired this early recovery, as shown by a significant impairment in the ability to retrieve pellets successfully out to 2 weeks after stroke (FIG. 7, panel D).

Positive AMPAR Modulation does not Alter Poststroke Axonal Sprouting

Figure 8:
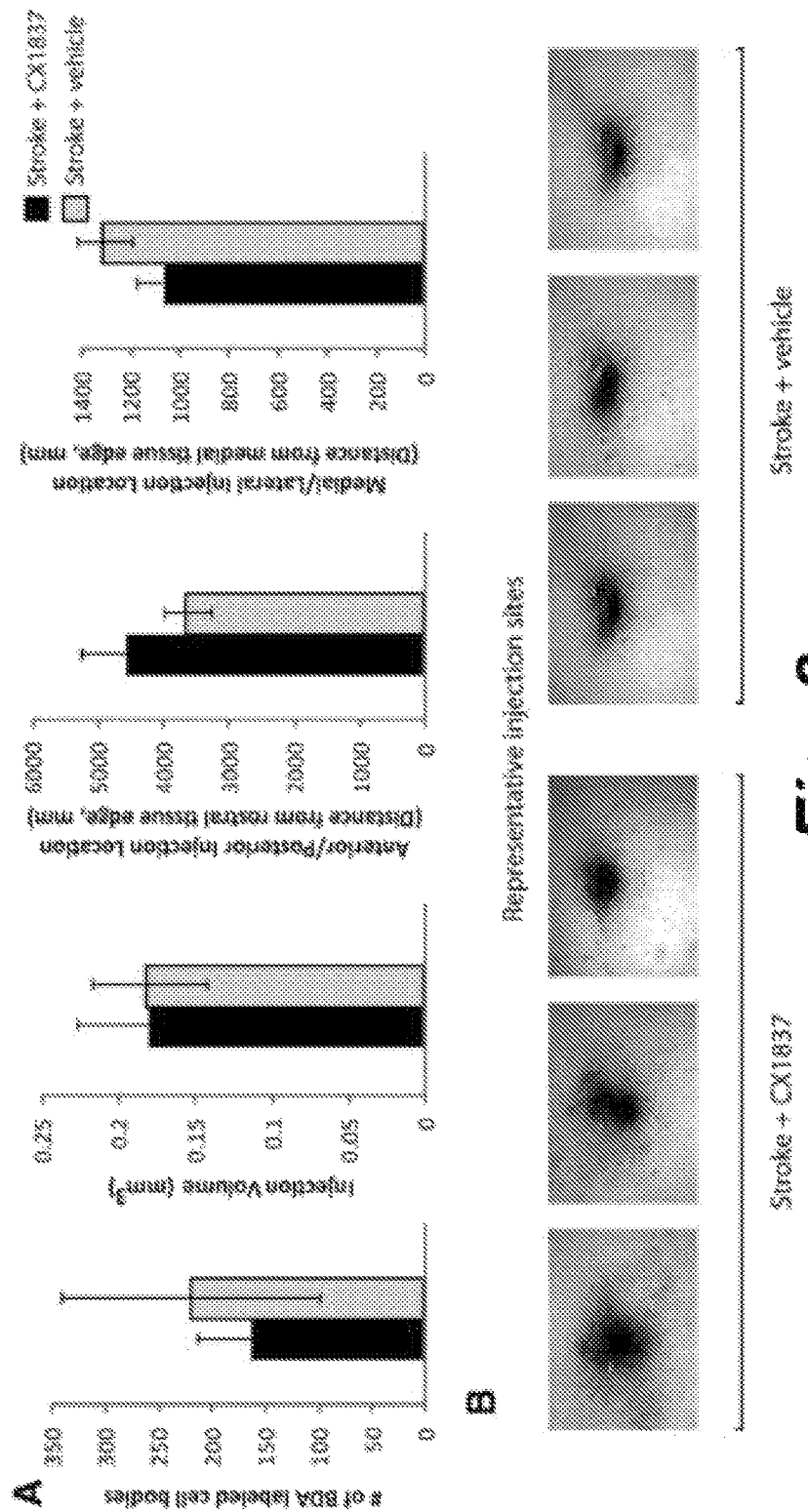
FIG. 8, panels A-C, show that BDA injection volume and location are uniform across experimental groups. There were no significant differences between the number of BDA-labeled cell bodies, BDA volumes, and location between stroke plus vehicle and stroke plus CX1837-treated animals (panel A). Photomicrographs show representative BDA injection sizes for three animals for stroke plus vehicle and stroke plus CX1837 (panel B). Sample photomicrographs show representative imaged of BDA-labeled cell bodies in somatosensory cortex (panel C). Data shown are averages±SEM for n=4 per group.
Figure 9:
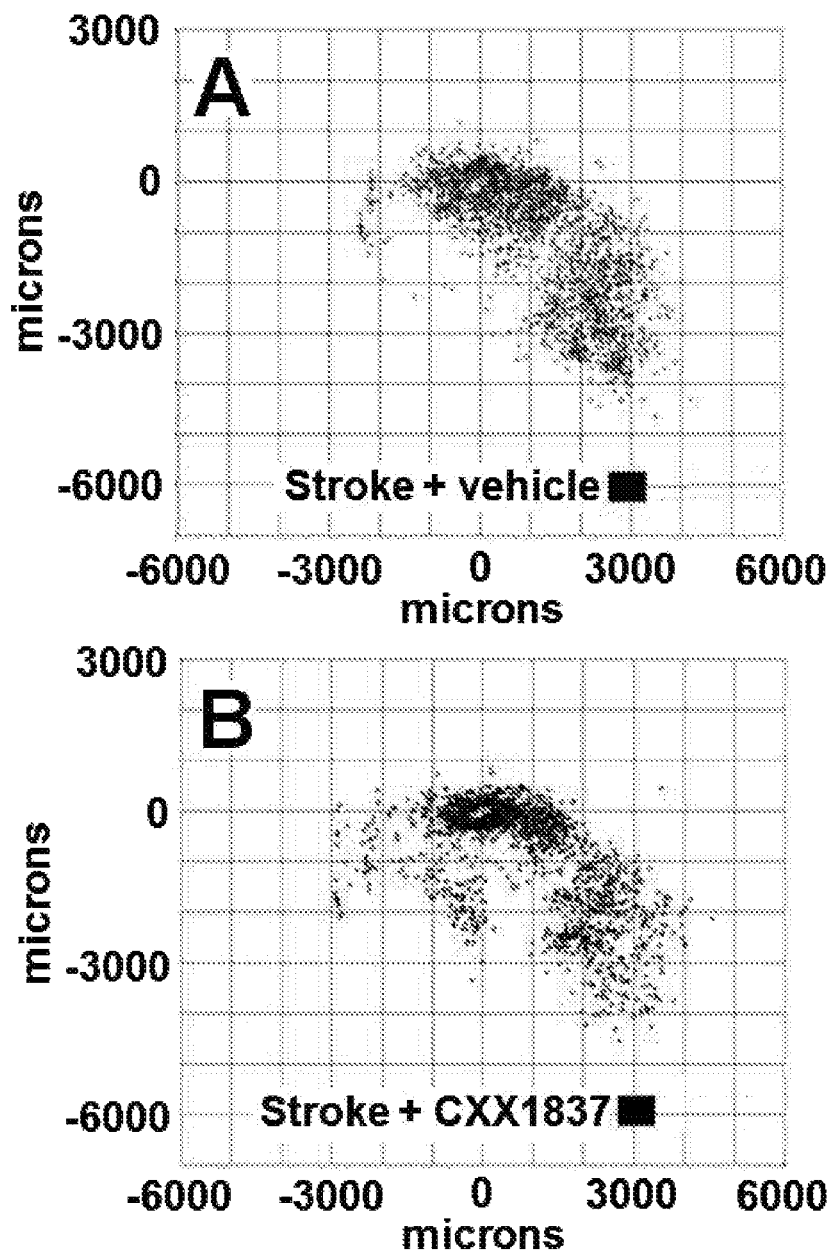
FIG. 9, panels A-D, show patterns of cortical connections in control and in conditions of AMPAR conductance. A small injection of the neuroanatomical tracer BDA was placed into the forelimb motor cortex adjacent to the stroke site 6 weeks after stroke. The location of all labeled cell bodies in the forelimb motor cortex, forelimb and hind limb somatosensory cortex, and facial (whisker) somatosensory cortex were digitally plotted. These plots convert the location of all the axonal connections of forelimb motor cortex into x/y plots, which are then grouped according to treatment condition and statistically compared among groups (Hotelling's inverseT matrix). The plots in panel A (stroke plus vehicle treatment) and panel B (stroke plus CX1837 treatment) show the location of labeled axons in groups of animals (n=4 for each condition). For CX1837-treated mice, there is no difference in the spatial distribution (panel C) relative to vehicle-treated stroke controls. Polar distribution plots, incorporating normalized axon quantity and distribution of axons in register with connectional plot (panel D). Shaded polygons (panel D) represent 70th percentile of the distances of labeled axons from the injection site in each segment of the graph.

The process of neural repair after stroke involves sprouting of new connections within the periinfarct cortex (Carmichael et al. (2001) *Neurobiol. Dis.,* 8: 910-922; Li et al. (2010) *Nat. Neurosci.* 13: 1496-1504). BDNF has its locus of action in periinfarct cortex (FIGS. 5, 6) and has been shown to have significant effects on neuronal sprouting (Batchelor et al. (2008) *Brain Res.,* 1209: 49-56). To assess whether the functional gains associated with CX1837-induced BDNF are linked to sprouting of new connections within the periinfarct region, we quantitatively mapped the motor cortex connections (Li et al. (2010) *Nat. Neurosci.* 13: 1496-1504) in stroke plus vehicle controls and stroke plus CX1837 treatment at the maximally effective dosing regimen (1 mg/kg, i.p., bid). The distribution of BDA-labeled cell bodies were mapped in x/y coordinates, registered to the somatosensory body map in tangential cortical sections, collapsed from individual animals to treatment groups, and statistically compared for changes in the pattern of motor cortex connections (FIG. 8). There was no significant difference in the pattern of motor system cortical connections between stroke-control and stroke plus CX1837 (FIG. 9).

Inflection Point in AMPA Effects on Stroke Size

Figure 10:
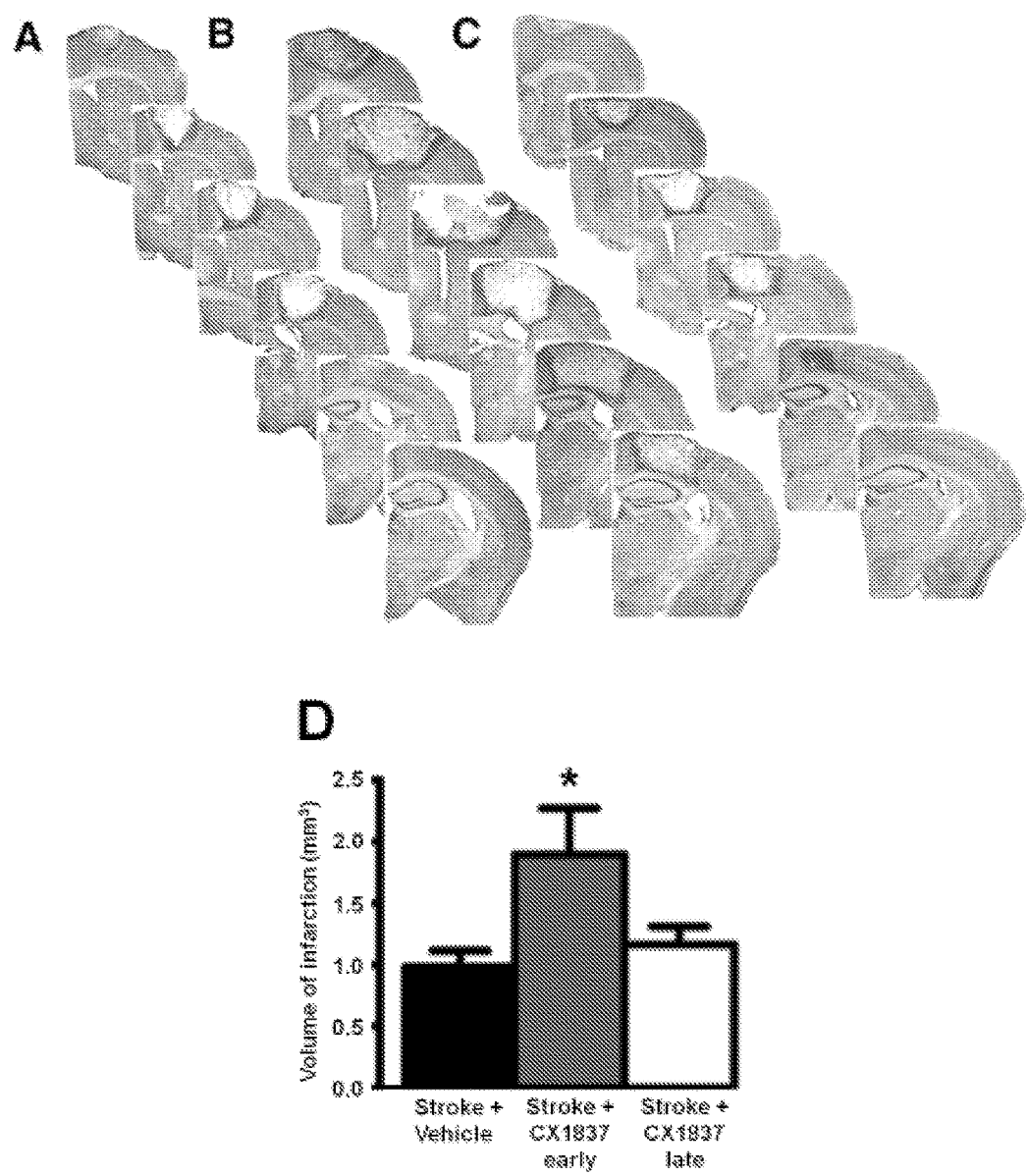
FIG. 10, panels A-D, show inflection point in CX1837 effect on infarct size. Representative Nissl-stained sections 7 d after stroke from stroke plus vehicle treatment (panel A), stroke plus CX1837 treatment starting at the time of stroke (panel B), and stroke plus CX1837 treatment starting from 5 d after insult (panel C). Quantification of the stroke volume is shown in panel D. Data are shown as mean±SEM for n=4 per group. *$p<0.05$.

Glutamate-induced excitotoxicity mediates early cell death after stroke (Lipton (1999) *Physiol. Rev.* 79: 1431-1568). Previous studies using AMPAR antagonists (Weiser (2005) *Curr. Drug Targets CNS Neurol. Disord.* 4: 153-159) have shown a decrease in stroke size in animals when treatments have started at the time of or shortly after stroke induction. Thus, positive modulation of the AMPAR may affect stroke size, particularly if given early after the stroke. Stroke volume was assessed 7 d after insult in mice that received stroke plus vehicle or CX1837 at the time of stroke, or beginning 5 d after stroke, which is the timing of the above studies for effective functional recovery. There was no significant difference in stroke volume between vehicle-treated and CX1837 treatment starting from 5 d after stroke (stroke plus vehicle, 0.98±0.13, vs stroke plus CX1837 late, 1.16±0.15) (FIG. 10). However, a significant increase in the volume of infarction was seen when treatment with CX1837 started at the time of induction of cerebral ischemia (stroke plus CX1837 early, 1.89±0.38; $p<0.05$) (FIG. 10).

Discussion

AMPAR function plays a critical but functionally contradictory role in the spectrum of stroke pathophysiology. AMPAR signaling in the tissue adjacent to the infarct mediates behavioral recovery of limb control over weeks after the stroke. This process occurs through BDNF induction in periinfarct cortex. Positive AMPAR modulation in a way that also induces BDNF promotes improved recovery of motor function during this recovery phase after stroke and blockade of AMPA signaling retards motor recovery. However, immediately after stroke, AMPARs are involved in cell death and infarct evolution. Positive AMPAR modulation increases infarct size immediately after stroke. These data indicate that there is an inflection point within the first several days after stroke where AMPAR signaling switches from promoting cell death to promoting behavioral recovery. Positive modulation of AMPAR signaling during stroke recovery is a novel pharmacological target to promote improved behavioral outcomes in this disease.

Learning and Memory and Stroke Recovery

Therapies that promote functional recovery after stroke are limited to physical rehabilitation measures, with a limited degree of recovery. There are no pharmacological therapies that stimulate recovery. There are parallels on many levels between mechanisms of learning and memory and those of functional recovery after stroke. Functional recovery after stroke follows psychological learning rules such as learned nonuse, mass action, contextual interference, and distributed practice (Krakauer (2006) *Curr. Opin. Neurol.,* 19: 84-90) that indicate learning and memory principles may underlie behavioral recovery. On a cellular level, memory formation is mediated by alterations in synaptic strength and structure, including LTP and dendritic spine morphogenesis (Bliss and Collingridge (1993) *Nature* 361: 31-39). Stroke increases the level of LTP-like cortical excitability Di Lazzaro et al. (2010) *Cereb. Cortex* 20: 1523-1528) and alters dendritic spine structure Brown et al. (2007) *J. Neurosci.,* 27: 4101-4109; Sigler et al. (2009) *Proc. Natl. Acad. Sci. U.S.A.,* 106: 11759-11764). These parallels between learning and memory and stroke recovery suggest that molecular memory systems may play a role in stroke recovery.

AMPAR signaling is one leading candidate for a common memory and stroke recovery system. AMPAR trafficking is important in the induction and maintenance of LTP (Derkach et al. (2007) *Nat. Rev. Neurosci.* 8: 101-113). Increased AMPAR signaling promotes neuronal remodeling and dendritic sprouting that underlies many aspects of learning and memory Lynch et al. (2008) *Eur. J. Pharmacol.* 585: 2-13). Here, we report that AMPAR signaling after stroke controls major aspects of motor recovery via an increase in local BDNF levels. We tested the effect of manipulating AMPAR and/or BDNF in two ways. First, we blocked AMPARs with CFM2. This transiently worsened recovery but did not have a generally negative effect on recovery in three different behavioral measures (FIG. 7). We then blocked all of BDNF signaling, by locally releasing TrkB-Fc. This blocked recovery in three measures. These findings disassociate AMPAR effects on recovery from BDNF effects. Blocking BDNF considerably disrupts recovery, indicating that it plays a more fundamental or downstream role on recovery after stroke from the AMPAR. This fits with a model in which positively modulating AMPAR signaling is one way to enhance BDNF effects but that there are likely other mechanisms in place for BDNF induction after stroke.

BDNF and Functional Recovery in Stroke

BDNF is an activity-dependent trophic factor that mediates many aspects of neuronal plasticity. BDNF mediates neuronal spine plasticity in a process that is thought to underlie LTP (Bramham (2008) Curr. Opin. Neurobiol., 18: 524-531; Ji et al. (2010) Nat. Neurosci., 13: 302-309). Additionally, BDNF directly modifies cortical map plasticity (Prakash et al. (1996) Nature 381: 702-706. Behavioral recovery in stroke is closely correlated with changes in cognitive, motor, and sensory maps. In human stroke patients, an expansion in motor representation maps is seen in tissue adjacent or connected to stroke (Carmichael (2006) Ann. Neurol. 59:7 35-742). In animal models, when stroke damages primary motor or somatosensory areas, motor and sensory representations remap in periinfarct cortex (Dijkhuizen et al. (2003) J. Neurosci., 23: 510-517; Brown et al. (2009) J. Neurosci., 29: 1719-1734), and these map alterations occur in regions of dendritic spine turnover (Brown et al. (2009) J. Neurosci., 29: 1719-1734). These parallels suggest that BDNF may support behavioral recovery after stroke.

Figure 11:
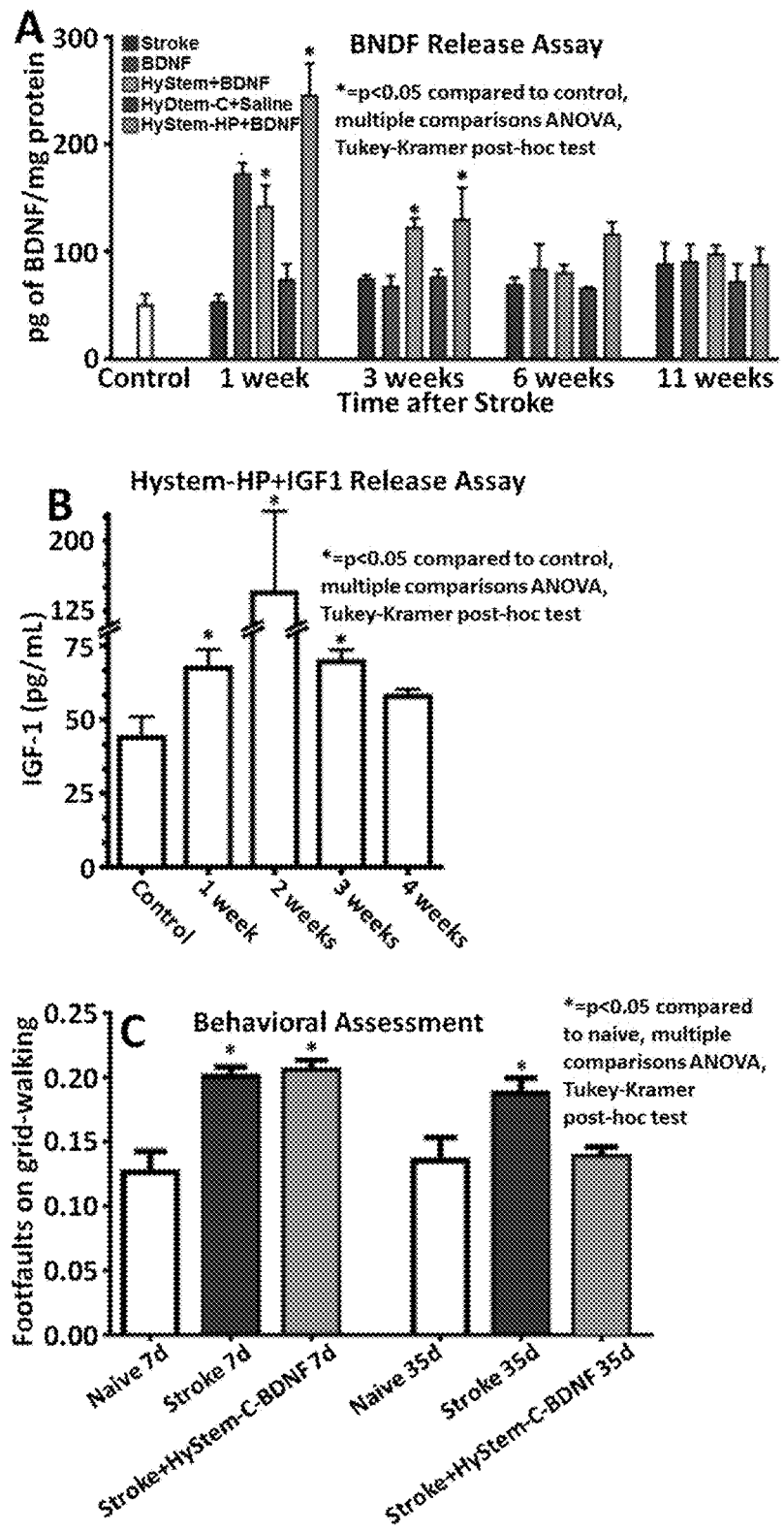
FIG. 11, panels A-C, show the slow release properties of BDNF from HYSTEM®-C® and HYSTEM®-HP, IGF1 release from HYSTEM®-HP and the improvement in functional recovery with this slow release of BDFN from HYSTEM®-C after stroke. Panel A: BDNF was suspended in HYSTEM®-C and then injected into normal brain. BDNF levels were determined via ELISA in unoperated control animals (no HYSTEM®-C or BDNF, "control" in figure) and at 1, 3, 6 and 11 weeks after injection. As a comparison to HYSTEM®-C, the same amount of BDNF was suspended into a second hyaluronan hydrogel, HyStem-HP®. BDNF was also directly injected into the brain, without either hydrogel. BDNF is slowly released by both HYSTEM®-C and HYSTEM®-HP at significant levels up to 3 weeks after stroke. Panel B: IGF1 was suspended into HyStem-HP and injected into the stroke cavity. Panel C: Recovery of forelimb movement control was measured in mice subjected to stroke and compared to unoperated (naïve) mice. Behavioral deficits in forelimb movement control were assessed in walking on a wire grid, by the number of times that the forelimb paw fell through the grid (footfault). HYSTEM®-C+BDNF was injected just after the first testing period, 7 days after stroke. 4 weeks after injection, and 5 weeks after stroke, HYSTEM®-C+BDNF improves functional recovery, such that the performance of mice with treatment is not different from naïve, non-stroke mice.

The present data show a clear role for BDNF signaling in behavioral recovery after stroke. Systemic administration of CX1837 induces BDNF levels and TrkB phosphorylation in periinfarct cortex. Local blockade of BDNF induction in periinfarct cortex not only prevents the ampakine-mediated behavioral recovery but also generally blocks motor recovery after stroke. Previous studies have shown that intravenous administration of BDNF Schabitz et al. (2004) Stroke 35: 992-997) improves behavioral outcome after stroke, and intraventricular infusion of BDNF antisense oligonucleotides (Ploughman et al. (2009) Stroke 40: 1490-1495) blocks aspects of recovery after stroke. To directly test the role of BDNF in recovery after stroke, BDNF was delivered in this stroke model discussed above (Clarkson et al. (2010) Nature 468: 305-309) through HYSTEM®-$^-$C delivery, started 7 days after the stroke. BDNF delivered in this way produces significant improvements in functional recovery weeks after the stroke (FIG. 11). The present data indicate that BDNF normally mediates motor recovery after stroke, localizes this effect to the periinfarct cortex adjacent to the stroke site, and identifies a systemic pharmacological therapy that will modulate BDNF in this critical periinfarct region for motor recovery. BDNF does not appear to induce an improvement in functional recovery through axonal sprouting. These data are the first to specifically localize motor recovery to one brain region after stroke, the periinfarct cortex. Furthermore, because BDNF is poorly permeable to the blood-brain barrier (Zhang and Pardridge (2006) Brain Res., 1111: 227-229) and likely to have significant toxicity if given systemically, ampakine administration provides a novel means of inducing BDNF within the periinfarct cortex via a systemic route.

Brain Excitability in Neural Repair and Functional Recovery after Stroke

The ability to regain function after stroke relies heavily on the ability of the brain to relearn motor and other tasks. This ability to relearn after stroke follows activity-dependent processes associated with motor learning and memory (Conner et al. (2005) Neuron 46: 173-179; Krakauer (2006) Curr. Opin. Neurol., 19: 84-90). As with stroke recovery, the processes of learning and memory can be enhanced by manipulations that increase neuronal excitability (Clarkson and Carmichael (2009) Biochem. Soc, Trans., 37: 1412-1414). For example, functional recovery in periinfarct cortex is aided by extrinsic manipulation of neuronal excitability, such as modulation of tonic GABA inhibitory currents (Clarkson et al. (2010) Nature 468: 305-309). Importantly, the pattern of behavioral recovery induced by blocking tonic GABA currents differs from that seen with positive modulation of AMPAR signaling. Antagonizing tonic GABA inhibition produces an early recovery and rapidly maximal recovery within the first week after stroke (Id.). However, positive allosteric modulation of AMPAR function produces a delayed and gradual recovery over 7 weeks (FIG. 2). These data indicate that blocking GABA tonic inhibition and facilitating AMPAR function produce two very different profiles of enhanced recovery, and ones that are specific to each approach.

There are other indications that modulation of cortical excitability impact functional recovery after stroke. Direct current stimulation of periinfarct cortex, using a protocol that boosts local neuronal excitability, improves use of the affected limb in stroke patients (Hummel and Cohen (2006) Lancet Neurol., 5: 708-712). Forced use and task specific repetitive movements of the affected limb have both been shown to activate the periinfarct cortex and aid in improved functional recovery. A recent report suggests that direct current stimulation may work in part via the enhanced release of BDNF (Cheeran et al. (2008) J. Physiol. 586: 5717-5725), a mechanism similar to what we find occurs here with the use of high-impact ampakines. The field of direct current stimulation and behavioral brain activation after stroke is evolving, but the cellular mechanisms underlying these therapies are not well understood. However, these data indicate that clinical therapies that alter the excitability of periinfarct cortex, either pharmacological as in the present data or electrical, may improve recovery after stroke and may be comparable with what is described here after treatment with ampakines.

Ampakines have been successfully shown to boost learning and memory function in normal animals, and in genetic models of cognitive diseases, such as Huntington's disease Simmons et al. (2009) Proc. Natl. Acad. Sci. U.S.A., 106: 4906-4911). We show for the first time that the BDNF-inducing ampakine CX1837 boosts motor recovery after stroke. This suggests that the similarities between neuronal mechanisms of learning and memory and those of functional recovery after stroke may extend more generally to common treatment strategies for both. Initial cell death and delayed neuronal recovery both occur through overlapping excitatory mechanisms. An important point from the present studies is that treatments that focus on manipulating molecular memory systems to alter excitatory signaling and recovery in the brain must be accomplished at specific delay points after the onset of stroke.

Example 2

BDNF Slow Released from a HYSTEM® Hydrogel

FIG. 11, panels A-C show the slow release properties of BDNF from HYSTEM®-C and HYSTEM®-HP®, IGF1 release from HYSTEM®-HP and the improvement in functional recovery with this slow release of BDFN from HYSTEM®-C after stroke. Panel A: BDNF was suspended in the soluble components of HYSTEM®-C prior to gelation by addition of the HYSTEM® crosslinker, and then injected into normal brain. BDNF levels were determined via ELISA in unoperated control animals (no HYSTEM®-C or BDNF, "control" in figure) and at 1, 3, 6 and 11 weeks after injection. As a comparison to HYSTEM®-C, the same amount of BDNF was suspended into a second hyaluronan hydrogel, HYSTEM®-HP. BDNF was also directly injected into the brain, without either hydrogel. BDNF is slowly released by both HYSTEM®-C and HYSTEM®-HP at significant levels up to 3 weeks after stroke. Panel B: IGF1 was suspended into HYSTEM®-HP and injected into the stroke cavity. Panel C: Recovery of forelimb movement control was measured in mice subjected to stroke and compared to unoperated (naïve) mice. Behavioral deficits in forelimb movement control were assessed in walking on a wire grid, by the number of times that the forelimb paw fell through the grid (footfault). HYSTEM®-C+BDNF was injected just after the first testing period, 7 days after stroke. 4 weeks after injection, and 5 weeks after stroke, HYSTEM®-C+BDNF improves functional recovery, such that the performance of mice with treatment is not different from naïve, non-stroke mice.

Example 3

Use of Clonal Human Embryonic Progenitor Cells in a Collagen-Hyaluronic Acid Hydrogel as a Means of the Delivery of Factors to Improve Stroke Recovery Human ES-derived clonal embryonic progenitor cell lines described herein designated SM22, CM02, and EN13 that are each capable of expressing BDNF, HBEGF, VEGFA, IGF1, and FGF2 (bFGF) and E33 that is capable of expressing BDNF, HBEGF, VEGFA, and FGF2 (bFGF) but not IGF1 were cultured in their respective optimized growth medium on 0.1% gelatin coated Corning tissue culture treated polystyrene flasks in a humidified incubator at 37° C. with 5% $O_2$ and 10% $CO_2$. On the day of injection the confluent cells were detached with Trypsin/EDTA. Upon detachment, growth media (containing serum) was added to deactivate trypsin and cell concentration was determined using a hemocytometer. Approximately 7.5 million cells were aliquoted and prepared for injections into the chemically injured brain regions of rats. The cells were pelleted by centrifugation, the supernatant was aspirated, and the pelleted cells were resuspended in HYSTEM®-C (hyaluronan and collagen-based hydrogel Cat. # GS311(BioTime, Alameda, Calif.) at $1\times10^5$ cells/µL. Fifteen microliters of the cell suspension were aliquoted into separate sterile microfuge tubes for a 10 ul injection containing $1\times10^6$ cells per rat. A total of 20 rats were utilized as follows: 1) 4 rats injected with 10 µL of vehicle control (HYSTEM®-C); 2) 4 rats each injected with $1\times10^6$ EN13 cells in 10 µL of HYSTEM®-C; 3) 4 rats each injected with $1\times10^6$ CM02 cells in 10 µL of HYSTEM®-C; 4) 4 rats each injected with $1\times10^6$ E33 cells in 10 µL of HYSTEM®-C; 5) 4 rats each injected with $1\times10^6$ SM22 cells in 10 µL of HYSTEM®-C. Cells were injected immediately following the induction of injury.

Recovery was assayed using Bederson's score, the limb-placing test, right-biased swing test, and a cylinder test for the use of the right forelimb. At 24 hours post treatment, there was a trend toward improved recovery in all of the cell-containing formulations compared to vehicle control. However, at 72 hours post treatment, there was a statistically significant improvement in all of the cell-containing formulations compared to vehicle control. For example, in the cylinder test for the use of the right forelimb, vehicle control showed a 0% use of the right forelimb, while the cell-containing formulations gave average values averaging approximately 30%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving recovery of a mammal after cerebral ischemia, said method comprising:
   administering a therapeutically effective amount of a hydrogel containing BDNF into the infarct cavity in the brain of said mammal, wherein said administering comprises depositing said hydrogel into said infarct cavity, wherein said hydrogel provides sustained release of said BDNF over time, and wherein said hydrogel is not administered until at least 7 days after the onset of the ischemic event.

2. The method of claim 1, wherein said hydrogel comprises a biopolymer.

3. The method of claim 2, wherein said hydrogel comprises one or more materials selected from the group consisting of hyaluronan, gelatin, thiol-modified hyaluronan, heparin, thiol-modified heparin, thiol-modified chondroitin sulfate, thiol-modified gelatin, a hyaluronan sodium salt, and an acrylated hyaluronic acid.

4. The method of claim 1, wherein said hydrogel comprises a hyaluronan derivative and a gelatin derivative.

5. The method of claim 4, wherein hyaluronan derivative comprises a thiolated hyaluronan.

6. The method of claim 4, wherein said gelatin derivative comprises a thiolated gelatin.

7. The method of claim 5, wherein said thiolated hyaluronan and thiolated gelatin have each been thiol-modified using carbodiimide mediated hydrazide chemistry.

8. The method of claim 4, wherein said hydrogel further comprises heparin or a heparin derivative.

9. The method of claim 8, wherein said hydrogel comprises a thiol-modified heparin.

10. The method of claim 1, wherein said administering comprises injecting said hydrogel into said ischemic cavity.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: Artificial
<220> FEATURE:
<223> OTHER INFORMATION: Synthetic peptide

<400> SEQUENCE: 1

Gly Cys Arg Asp Gly Pro Gln Gly Ile Trp Gly Gln Asp Arg Cys Gly
1               5                   10                  15

<210> SEQ ID NO 2
<211> LENGTH: 16
<212> TYPE: PRT
<213> ORGANISM: Artificial
<220> FEATURE:
<223> OTHER INFORMATION: Synthetic peptide

<400> SEQUENCE: 2

Gly Cys Arg Asp Gly Asp Gln Gly Ile Ala Gly Phe Asp Arg Cys Gly
1               5                   10                  15